US009826972B2

(12) United States Patent
Ranucci et al.

(10) Patent No.: US 9,826,972 B2
(45) Date of Patent: Nov. 28, 2017

(54) INSTRUMENTS FOR DELIVERING TRANSFASCIAL SUTURES, TRANSFASCIAL SUTURE ASSEMBLIES AND METHODS OF TRANSFASCIAL SUTURING

(71) Applicant: C.R. Bard, Inc., Murray Hill, NJ (US)

(72) Inventors: Kevin J. Ranucci, Warwick, RI (US); Roger E. Darois, Foster, RI (US); Donald E. Ziniti, Cumberland, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 203 days.

(21) Appl. No.: 14/353,938

(22) PCT Filed: Oct. 23, 2012

(86) PCT No.: PCT/US2012/061416
§ 371 (c)(1),
(2) Date: Apr. 24, 2014

(87) PCT Pub. No.: WO2013/062933
PCT Pub. Date: May 2, 2013

(65) Prior Publication Data
US 2014/0296881 A1   Oct. 2, 2014

Related U.S. Application Data

(60) Provisional application No. 61/550,735, filed on Oct. 24, 2011.

(51) Int. Cl.
*A61B 17/04*   (2006.01)
*A61F 2/00*    (2006.01)
*A61B 17/06*   (2006.01)

(52) U.S. Cl.
CPC .. *A61B 17/0401* (2013.01); *A61B 2017/0404* (2013.01); *A61B 2017/0409* (2013.01);
(Continued)

(58) Field of Classification Search
CPC ............ A61B 17/0401; A61B 17/0409; A61B 17/0411; A61B 17/0412; A61B 17/0469;
(Continued)

(56) References Cited

U.S. PATENT DOCUMENTS

| | | |
|---|---|---|
| 4,235,238 A | 11/1980 | Ogiu et al. |
| 4,696,300 A | 9/1987 | Anderson |

(Continued)

FOREIGN PATENT DOCUMENTS

| | | |
|---|---|---|
| DE | 197 07 851 A1 | 9/1998 |
| EP | 1 762 185 A1 | 3/2007 |

(Continued)

OTHER PUBLICATIONS

Office Action for U.S. Appl. No. 13/290,236, dated Dec. 14, 2015 (11 pages).

(Continued)

*Primary Examiner* — David C Eastwood
*Assistant Examiner* — Kankindi Rwego
(74) *Attorney, Agent, or Firm* — Wolf, Greenfield & Sacks, P.C.

(57) ABSTRACT

A method of transfascial suturing may include delivering a suture assembly into an abdominal cavity of a patient, passing a suture anchor, from within the abdominal cavity, through a soft tissue repair prosthetic provided in the abdominal cavity and then through the abdominal wall to a location either above or below the skin, and tightening the suture assembly. An instrument for transfascial suturing may include a handle, a shaft extending from the handle, and a drive system for advancing a suture or suture assembly out of the instrument and across the fascia. The instrument may advance a suture anchor and a suture from within the abdominal cavity and across the abdominal wall to present the suture anchor on the opposite side of the fascia. The (Continued)

instrument may be adapted to present the suture anchor either above or below the skin surface for subsequent tightening of the suture assembly.

37 Claims, 20 Drawing Sheets

(52) U.S. Cl.
CPC ............... *A61B 2017/0417* (2013.01); *A61B 2017/0419* (2013.01); *A61B 2017/0427* (2013.01); *A61B 2017/0462* (2013.01); *A61B 2017/06176* (2013.01); *A61F 2/0063* (2013.01)

(58) Field of Classification Search
CPC ...... A61B 2017/074; A61B 2017/0403; A61B 2017/0404; A61B 2017/0406; A61B 2017/0417; A61B 2017/0419; A61B 2017/0425; A61B 2017/0446; A61B 2017/0448; A61B 2017/0462; A61B 2017/0464; A61B 2017/0466; A61B 2017/047; A61B 2017/0472; A61B 2017/0474; A61B 2017/0475; A61B 2017/0477; A61B 2017/0479; A61B 2017/048; A61B 2017/0488; A61B 2017/049; A61B 17/0487; A61F 2/0063; A61F 2002/0072; A61F 2002/0068
See application file for complete search history.

(56) References Cited

U.S. PATENT DOCUMENTS

| | | |
|---|---|---|
| 4,750,492 A | 6/1988 | Jacobs |
| 4,935,027 A | 6/1990 | Yoon |
| RE34,021 E | 8/1992 | Mueller et al. |
| 5,203,787 A | 4/1993 | Noblitt et al. |
| 5,226,426 A | 7/1993 | Yoon |
| 5,269,809 A | 12/1993 | Hayhurst et al. |
| 5,281,237 A | 1/1994 | Gimpelson |
| 5,290,217 A | 3/1994 | Campos |
| 5,290,297 A | 3/1994 | Phillips |
| 5,366,480 A | 11/1994 | Corriveau et al. |
| 5,372,146 A | 12/1994 | Branch |
| 5,403,329 A | 4/1995 | Hinchcliffe |
| 5,403,348 A | 4/1995 | Bonutti |
| 5,411,520 A | 5/1995 | Nash et al. |
| 5,470,337 A | 11/1995 | Moss |
| 5,496,348 A | 3/1996 | Bonutti |
| 5,500,000 A | 3/1996 | Feagin et al. |
| 5,501,692 A | 3/1996 | Riza |
| 5,507,754 A | 4/1996 | Green et al. |
| 5,520,691 A | 5/1996 | Branch |
| 5,522,846 A | 6/1996 | Bonutti |
| 5,527,343 A | 6/1996 | Bonutti |
| 5,534,012 A | 7/1996 | Bonutti |
| 5,549,631 A | 8/1996 | Bonutti |
| 5,569,305 A | 10/1996 | Bonutti |
| 5,593,422 A | 1/1997 | Muijs Van de Moer et al. |
| 5,618,290 A | 4/1997 | Toy et al. |
| 5,620,461 A | 4/1997 | Muijs Van De Moer et al. |
| 5,626,614 A | 5/1997 | Hart |
| 5,643,319 A | 7/1997 | Green et al. |
| 5,713,910 A | 2/1998 | Gordon et al. |
| 5,733,306 A | 3/1998 | Bonutti |
| 5,772,672 A | 6/1998 | Toy et al. |
| 5,810,848 A | 9/1998 | Hayhurst |
| 5,814,072 A | 9/1998 | Bonutti |
| 5,817,111 A | 10/1998 | Riza |
| 5,845,645 A | 12/1998 | Bonutti |
| 5,857,999 A | 1/1999 | Quick et al. |
| 5,868,762 A | 2/1999 | Cragg et al. |
| 5,904,692 A | 5/1999 | Steckel et al. |
| 5,941,900 A | 8/1999 | Bonutti |
| 5,944,739 A | 8/1999 | Zlock et al. |
| 5,948,002 A | 9/1999 | Bonutti |
| 5,954,747 A | 9/1999 | Clark |
| 5,964,773 A | 10/1999 | Greenstein |
| 6,022,360 A | 2/2000 | Reimels et al. |
| 6,056,773 A | 5/2000 | Bonutti |
| 6,117,160 A | 9/2000 | Bonutti |
| RE36,974 E | 11/2000 | Bonutti |
| 6,159,234 A | 12/2000 | Bonutti et al. |
| 6,210,416 B1 | 4/2001 | Chu et al. |
| 6,287,317 B1 | 9/2001 | Makower et al. |
| 6,293,952 B1 | 9/2001 | Brosens et al. |
| 6,306,159 B1 | 10/2001 | Schwartz et al. |
| 6,319,263 B1 | 11/2001 | Levinson |
| 6,428,562 B2 | 8/2002 | Bonutti |
| 6,464,713 B2 | 10/2002 | Bonutti |
| 6,500,184 B1 | 12/2002 | Chan et al. |
| 6,500,195 B2 | 12/2002 | Bonutti |
| 6,506,197 B1 | 1/2003 | Rollero et al. |
| 6,551,333 B2 | 4/2003 | Kuhns et al. |
| 6,554,845 B1 | 4/2003 | Fleenor et al. |
| 6,565,590 B2 | 5/2003 | Kieturakis et al. |
| 6,592,609 B1 | 7/2003 | Bonutti |
| 6,596,014 B2 | 7/2003 | Levinson et al. |
| 6,626,930 B1 | 9/2003 | Allen et al. |
| 6,635,073 B2 | 10/2003 | Bonutti |
| 6,638,286 B1 | 10/2003 | Burbank et al. |
| 6,692,506 B1 | 2/2004 | Ory et al. |
| 6,699,263 B2 | 3/2004 | Cope |
| 6,779,701 B2 | 8/2004 | Bailly et al. |
| 6,780,198 B1 | 8/2004 | Gregoire et al. |
| 6,821,285 B2 | 11/2004 | Laufer et al. |
| 6,966,916 B2 | 11/2005 | Kumar |
| 6,981,983 B1 | 1/2006 | Rosenblatt et al. |
| 7,021,316 B2 * | 4/2006 | Leiboff ............ A61B 17/0401 128/898 |
| 7,041,120 B2 | 5/2006 | Li et al. |
| 7,087,073 B2 | 8/2006 | Bonutti |
| 7,147,652 B2 | 12/2006 | Bonutti et al. |
| 7,150,750 B2 | 12/2006 | Damarati |
| 7,153,312 B1 | 12/2006 | Torrie |
| 7,320,701 B2 | 1/2008 | Haut et al. |
| 7,442,198 B2 | 10/2008 | Gellman et al. |
| 7,608,092 B1 | 10/2009 | Schaffhausen |
| 7,618,449 B2 | 11/2009 | Tremulis et al. |
| 7,722,629 B2 | 5/2010 | Chambers |
| 7,722,633 B2 | 5/2010 | Laufer et al. |
| 7,740,638 B2 | 6/2010 | Hyde |
| 7,815,659 B2 | 10/2010 | Conlon et al. |
| 7,846,179 B2 | 12/2010 | Belef et al. |
| 7,850,712 B2 | 12/2010 | Conlon et al. |
| 7,879,048 B2 | 2/2011 | Bain |
| 7,942,886 B2 | 5/2011 | Alvarado |
| 7,959,640 B2 | 6/2011 | Kantsevoy et al. |
| 8,512,375 B2 | 8/2013 | Torrie et al. |
| 8,702,753 B2 | 4/2014 | Mikkaichi et al. |
| 8,790,356 B2 | 7/2014 | Darois et al. |
| 9,039,721 B2 | 5/2015 | Ziniti et al. |
| 9,078,648 B2 | 7/2015 | Ziniti et al. |
| 9,393,007 B2 | 7/2016 | Darois et al. |
| 9,439,643 B2 | 9/2016 | Darois et al. |
| 2001/0021856 A1 | 9/2001 | Bolduc et al. |
| 2002/0019649 A1 | 2/2002 | Sikora et al. |
| 2002/0103494 A1 * | 8/2002 | Pacey ............... A61F 2/0063 606/151 |
| 2003/0045891 A1 | 3/2003 | Yamamoto et al. |
| 2003/0105489 A1 | 6/2003 | Eichhorn et al. |
| 2003/0181800 A1 | 9/2003 | Bonutti |
| 2003/0236535 A1 | 12/2003 | Onuki |
| 2004/0044364 A1 | 3/2004 | DeVries et al. |
| 2004/0092969 A1 | 5/2004 | Kumar |
| 2004/0133238 A1 | 7/2004 | Cerier |
| 2004/0138676 A1 | 7/2004 | Crabtree |
| 2004/0138683 A1 | 7/2004 | Shelton et al. |
| 2005/0019368 A1 | 1/2005 | Cook et al. |
| 2005/0033363 A1 | 2/2005 | Bojarski et al. |
| 2005/0043746 A1 | 2/2005 | Pollak et al. |
| 2005/0049635 A1 | 3/2005 | Leiboff |
| 2005/0075654 A1 | 4/2005 | Kelleher |

(56) References Cited

U.S. PATENT DOCUMENTS

| | | |
|---|---|---|
| 2005/0216059 A1 | 9/2005 | Bonutti et al. |
| 2006/0020247 A1 | 1/2006 | Kagan et al. |
| 2006/0025819 A1 | 2/2006 | Nobis et al. |
| 2006/0030868 A1 | 2/2006 | Bennett |
| 2006/0069399 A1 | 3/2006 | Weisel et al. |
| 2006/0116718 A1 | 6/2006 | Leiboff |
| 2006/0142784 A1 | 6/2006 | Kontos |
| 2006/0178680 A1 | 8/2006 | Nelson et al. |
| 2006/0265009 A1 | 11/2006 | Bonutti |
| 2006/0265011 A1 | 11/2006 | Bonutti |
| 2006/0271101 A1 | 11/2006 | Saadat et al. |
| 2006/0276871 A1 | 12/2006 | Lamson et al. |
| 2006/0293709 A1 | 12/2006 | Bojarski et al. |
| 2007/0049970 A1 | 3/2007 | Belef et al. |
| 2007/0073319 A1 | 3/2007 | Mikkaichi et al. |
| 2007/0149987 A1 | 6/2007 | Wellman et al. |
| 2007/0150002 A1 | 6/2007 | Szabo et al. |
| 2007/0156175 A1 | 7/2007 | Weadock et al. |
| 2007/0185532 A1 | 8/2007 | Stone et al. |
| 2007/0191886 A1 | 8/2007 | Dejima et al. |
| 2007/0203507 A1 | 8/2007 | McLaughlin et al. |
| 2007/0255306 A1 | 11/2007 | Conlon et al. |
| 2007/0276408 A1 | 11/2007 | Filipi et al. |
| 2007/0276414 A1 | 11/2007 | Nobles |
| 2007/0293876 A1 | 12/2007 | Abe et al. |
| 2008/0009888 A1 | 1/2008 | Ewers et al. |
| 2008/0039889 A1 | 2/2008 | Lamson et al. |
| 2008/0051836 A1 | 2/2008 | Foerster et al. |
| 2008/0066765 A1 | 3/2008 | Paraschac et al. |
| 2008/0114378 A1 | 5/2008 | Matsushita |
| 2008/0114399 A1 | 5/2008 | Bonutti |
| 2008/0140092 A1 | 6/2008 | Stone et al. |
| 2008/0140116 A1 | 6/2008 | Bonutti |
| 2008/0140117 A1 | 6/2008 | Bonutti et al. |
| 2008/0154286 A1 | 6/2008 | Abbott et al. |
| 2008/0161850 A1 | 7/2008 | Weisenburgh et al. |
| 2008/0177288 A1 | 7/2008 | Carlson |
| 2008/0228198 A1 | 9/2008 | Traynor et al. |
| 2008/0228265 A1 | 9/2008 | Spence et al. |
| 2008/0228266 A1 | 9/2008 | McNamara et al. |
| 2008/0255591 A1 | 10/2008 | Harada et al. |
| 2008/0294001 A1 | 11/2008 | Surti |
| 2009/0023997 A1 | 1/2009 | Stokes et al. |
| 2009/0062743 A1 | 3/2009 | Rotella et al. |
| 2009/0069823 A1 | 3/2009 | Foerster et al. |
| 2009/0082806 A1 | 3/2009 | West, Jr. et al. |
| 2009/0088780 A1 | 4/2009 | Shiono et al. |
| 2009/0088797 A1 | 4/2009 | Crombie et al. |
| 2009/0118734 A1 | 5/2009 | Bhatnagar et al. |
| 2009/0156997 A1* | 6/2009 | Trenhaile .............. A61F 2/0063 604/99.01 |
| 2009/0171140 A1 | 7/2009 | Chu |
| 2009/0192439 A1 | 7/2009 | Lamson et al. |
| 2009/0204147 A1 | 8/2009 | Rahmani |
| 2009/0216253 A1 | 8/2009 | Bell et al. |
| 2009/0216265 A1 | 8/2009 | DeVries et al. |
| 2009/0275961 A1 | 11/2009 | Harris et al. |
| 2009/0281568 A1* | 11/2009 | Cendan .............. A61B 17/0401 606/217 |
| 2009/0312603 A1 | 12/2009 | Lam et al. |
| 2009/0326566 A1 | 12/2009 | Alvarado |
| 2010/0010448 A1 | 1/2010 | Deckard |
| 2010/0030236 A1 | 2/2010 | Hayashi et al. |
| 2010/0036395 A1 | 2/2010 | Miller |
| 2010/0042114 A1 | 2/2010 | Schaffhausen |
| 2010/0069930 A1 | 3/2010 | Roslin et al. |
| 2010/0076462 A1 | 3/2010 | Bakos et al. |
| 2010/0106166 A1 | 4/2010 | Cropper et al. |
| 2010/0121353 A1 | 5/2010 | Marshall et al. |
| 2010/0174299 A1 | 7/2010 | Viola et al. |
| 2010/0234854 A1 | 9/2010 | Abbott et al. |
| 2010/0249809 A1 | 9/2010 | Singhatat et al. |
| 2010/0262166 A1 | 10/2010 | Boraiah et al. |
| 2010/0292712 A1 | 11/2010 | Nering et al. |
| 2010/0292719 A1 | 11/2010 | Ducharme |
| 2010/0324573 A1 | 12/2010 | Toubia et al. |
| 2011/0029012 A1 | 2/2011 | Tegels |
| 2011/0082472 A1 | 4/2011 | Harris et al. |
| 2011/0112434 A1 | 5/2011 | Ghabrial et al. |
| 2011/0125189 A1 | 5/2011 | Stoll, Jr. et al. |
| 2011/0166598 A1 | 7/2011 | Gonazles et al. |
| 2011/0306989 A1 | 12/2011 | Darois et al. |
| 2011/0306990 A1 | 12/2011 | Darois et al. |
| 2011/0306992 A1 | 12/2011 | Darois et al. |
| 2012/0035626 A1 | 2/2012 | Chu |
| 2012/0143220 A1 | 6/2012 | Morgan et al. |
| 2012/0143221 A1 | 6/2012 | Weisel et al. |
| 2012/0203276 A1 | 8/2012 | Darois et al. |
| 2013/0116708 A1 | 5/2013 | Ziniti et al. |
| 2013/0116709 A1 | 5/2013 | Ziniti et al. |
| 2013/0116710 A1 | 5/2013 | Ziniti et al. |
| 2016/0317145 A1 | 11/2016 | Darois et al. |
| 2016/0338692 A1 | 11/2016 | Darois et al. |

FOREIGN PATENT DOCUMENTS

| | | |
|---|---|---|
| EP | 1 769 749 A1 | 4/2007 |
| EP | 1 808 134 A2 | 7/2007 |
| JP | 5-161655 A | 6/1993 |
| WO | WO 98/46142 A1 | 10/1998 |
| WO | WO 99/45848 A1 | 9/1999 |
| WO | WO 02/053011 A2 | 7/2002 |
| WO | WO 2004/008973 A1 | 1/2004 |
| WO | WO 2004/098415 A2 | 11/2004 |
| WO | WO 2009/049002 A1 | 4/2009 |
| WO | WO 2011/014244 A1 | 2/2011 |
| WO | WO 2011/041571 A2 | 4/2011 |
| WO | WO 2011/123714 A1 | 10/2011 |

OTHER PUBLICATIONS

Office Action for U.S. Appl. No. 13/157,172, dated Jan. 6, 2016 (12 pages).
Office Action for U.S. Appl. No. 13/157,182, dated Aug. 19, 2015 (12 pages).
Final Office Action for U.S. Appl. No. 13/157,172, dated Aug. 31, 2015 (12 pages).
Office Action for U.S. Appl. No. 13/157,155, dated Sep. 9, 2015 (18 pages).
Invitation to Pay Additional Fees and Communication Relating to the Results of the Partial International Search dated Sep. 12, 2011 for PCT/US2011/039793.
International Search Report and Written Opinion dated Dec. 20, 2011 for International Application No. PCT/US2011/039793.
International Search Report and Written Opinion dated Jan. 8, 2013 for PCT/US2012/061416.
International Search Report and Written Opinion dated May 8, 2014 for PCT/US2012/061416.
Final Office Action for U.S. Appl. No. 13/157,182, dated Jul. 5, 2013.
Final Office Action for U.S. Appl. No. 13/290,222 dated Dec. 4, 2013.
Office Action for U.S. Appl. No. 13/157,172 dated Oct. 18, 2013.
Office Action for U.S. Appl. No. 13/157,155, dated Jan. 3, 2014.
Office Action for U.S. Appl, No. 13/157,172 dated Apr. 3, 2014.
Office Action for U.S. Appl. No. 13/157,182 dated Oct. 10, 2012.
Office Action for U.S. Appl. No. 13/290,222 dated Apr. 2, 2013.
Office Action for U.S. Appl. No. 13/416,740 dated Oct. 25, 2013.
Interview Summary for U.S. Appl. No. 13/416,740 dated Feb. 21, 2014.
Office Action for U.S. Appl. No. 13/157,182, dated Aug. 5, 2014 (12 pages).
Office Action for U.S. Appl. No. 13/157,172, dated Aug. 12, 2014 (13 pages).
Office Action for U.S. Appl. No. 13/290,247, dated Oct. 3, 2014 (13 pages).
Office Action for U.S. Appl. No. 13/157,172 dated Feb. 12, 2015 (8 pages).

(56) References Cited

OTHER PUBLICATIONS

Final Office Action for U.S. Appl. No. 13/157,182, dated Feb. 25, 2015 (14 pages).
Final Office Action for U.S. Appl. No. 13/157,155, dated Oct. 14, 2014 (23 pages).
Office Action for U.S. Appl. No. 13/290,222, dated Oct. 31, 2014 (19 pages).
Office Action for U.S. Appl. No. 13/290,236, dated Aug. 10, 2016. 12 pages.
Office Action for U.S. Appl. No. 13/290,236, dated Mar. 2, 2017. 14 pages.

* cited by examiner

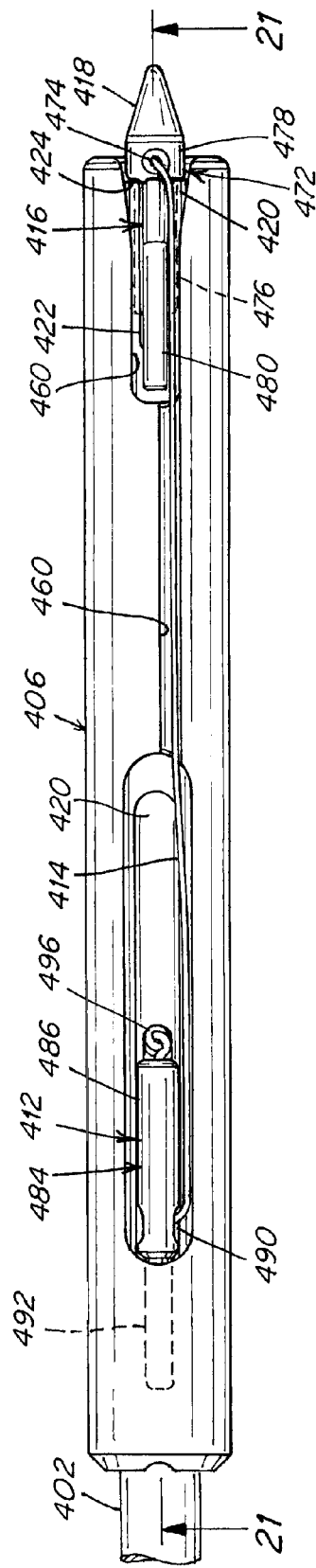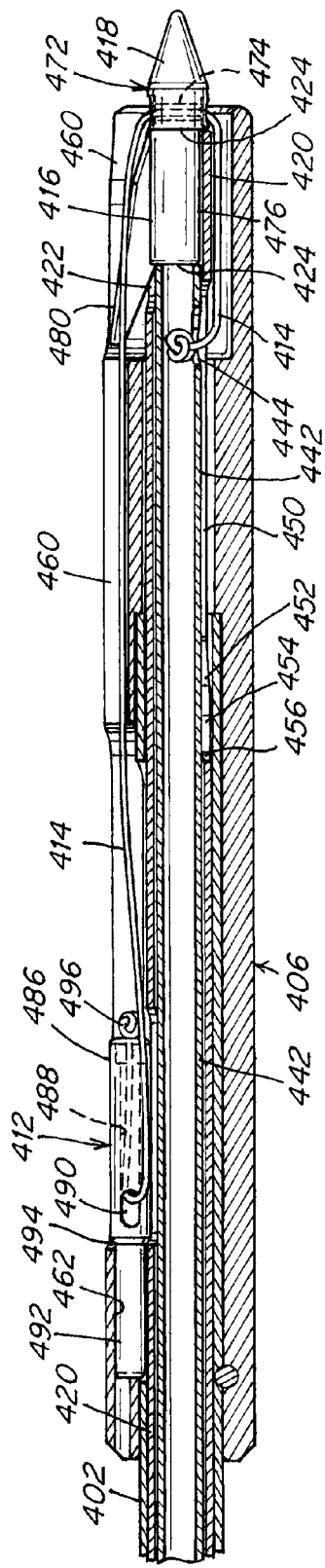
Fig. 20
Fig. 21

US 9,826,972 B2

INSTRUMENTS FOR DELIVERING TRANSFASCIAL SUTURES, TRANSFASCIAL SUTURE ASSEMBLIES AND METHODS OF TRANSFASCIAL SUTURING

RELATED CASE INFORMATION

This application is a 371 U.S. National Stage of International Application No. PCT/US2012/061416, filed on Oct. 23, 2012, which claims the benefit of U.S. provisional application No. 61/550,735, filed on Oct. 24, 2011, both of which are incorporated by reference herein in their entirety.

FIELD

The invention relates to instruments for delivering transfascial sutures, to transfascial suture assemblies and to methods of transfascial suturing.

BACKGROUND

Ventral hernia repair routinely involves placement of a soft tissue repair prosthetic, typically in the form of a patch, across an abdominal wall defect. In a laparoscopic procedure, or other minimally invasive approach, the patch is reduced in size and delivered through a narrow cannula or incision into the abdominal cavity where it then is returned to an expanded shape and deployed against the abdominal wall. Sutures may be applied through a partial, if not full, thickness of the abdominal wall (i.e., transfascial suturing). Additionally, or alternatively, tacks, screws, coils or other fasteners may be placed through the patch into just the innermost layers of the abdominal wall, such as the peritoneum and posterior fascia.

A conventional approach for transfascial suture delivery, as shown in FIG. 1, proceeds from outside of the patient. Sutures are pre-tied at spaced locations 100 about a patch 102 periphery, with pairs of suture tails 104 extending from each knot. It is these tails that will bridge the fascia and be secured together to form the transfascial suture fixation. The patch, preloaded with sutures, is collapsed and delivered into the abdominal cavity.

A suture passer instrument 106 is inserted, from outside of the patient, through the abdominal wall 108 and into the abdominal cavity in the approximate location of a particular suture tail pair. The suture passer includes a jaw or other grasper type arrangement which is operated within the cavity to capture one of the suture tails. The suture passer is retracted back through and out of the abdominal wall, drawing the suture tail exteriorly of the abdominal cavity. A hemostat or other clamp is applied to the exposed suture tail, preventing slippage of the suture tail back into the abdominal cavity. The suture passer is inserted again through the abdominal wall, creating a new puncture adjacent the first puncture, and operated to grab the remaining suture tail. The suture passer is pulled outwardly from the abdominal cavity, retrieving the second suture tail which also can be clamped against the anterior fascia. This standard transfascial suturing technique, approached from outside of the abdominal cavity, is repeated until all of the suture tail pairs have been transfascially deployed and tied together, typically at small skin incisions such that the tied knots are in the subcutaneous space.

SUMMARY

One aspect of the invention is a method of transfascial suturing. The method comprises acts of (a) delivering a suture assembly into an abdominal cavity of a patient, the suture assembly including a suture anchor, a force distribution member and a suture connected to the suture anchor and the force distribution member; (b) passing the suture anchor, from within the abdominal cavity, through a soft tissue repair prosthetic provided in the abdominal cavity and then through the abdominal wall to a location above the skin surface with the force distribution member being maintained in the abdominal cavity; and (c) tightening the suture assembly by advancing the suture anchor along the suture from the location above the skin surface to a position below the skin surface.

Another aspect of the invention is a method of transfascial suturing. The method comprises acts of (a) delivering a suture assembly into an abdominal cavity of a patient, the suture assembly including a suture anchor, a force distribution member and a suture connected to the suture anchor and the force distribution member; (b) passing the suture anchor, from within the abdominal cavity, through a soft tissue repair prosthetic provided in the abdominal cavity and then through at least a portion of the abdominal wall to a location below the skin surface without penetrating the skin surface and with the force distribution member being maintained in the abdominal cavity; and (c) tightening the suture assembly.

BRIEF DESCRIPTION OF DRAWINGS

The foregoing and other objects and advantages of the invention will be appreciated more fully from the following drawings, wherein like reference characters designate like features, in which:

FIGS. 18-23 are illustrations of an instrument for subdermal transfascial delivery of a suture assembly;

FIG. 23A is an enlarged detail view of the area encircled by arrow 23A-23A of FIG. 23;

DETAILED DESCRIPTION

Figure 1:
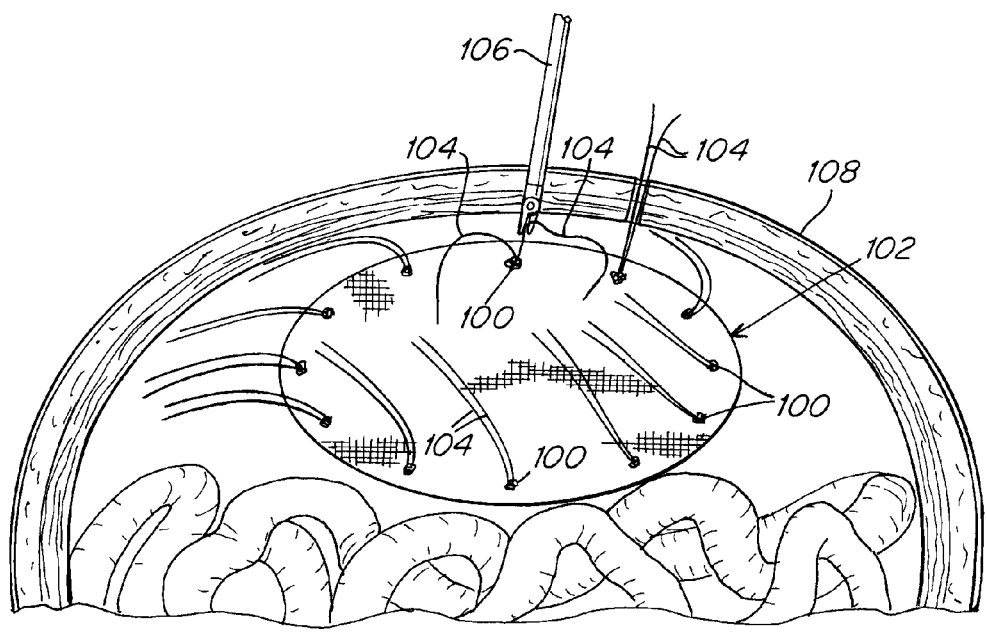
FIG. 1 is an illustration of a conventional transfascial suture delivery.

Various aspects of the invention are described below and/or shown in the drawings. These aspects of the invention may be used alone and/or in any suitable combination with each other. Aspects of the invention are not limited in any way by the illustrative embodiments shown and described herein.

Embodiments of the invention are described in connection with instruments for transfascial delivery of one or more sutures or suture assemblies, arrangements of transfascial suture assemblies, and methods of delivering a transfascial suture or suture assembly. These instruments, suture assemblies and methodologies are particularly configured for transfascial delivery of suture or suture assembly from within the abdominal cavity, rather than in the traditional manner of pulling suture across the fascia in an approach from outside of the patient. Such instruments, suture assemblies and techniques may be applied independently or in conjunction with other approaches, such as those involving mechanical fastener-type fixation. Although disclosed in connection with a repair of a ventral hernia, the invention is not so limited and has other applications as should be apparent to one of skill in the art.

An instrument for transfascial delivery of suture or a suture assembly may include an actuating handle, an elongated shaft extending from the handle, and a drive system for advancing a suture or suture assembly out of the instrument and across the fascia. The shaft may be relatively rigid or flexible, fixed or moveable relative to the handle, and may be sized to fit through a narrow cannula, such as a 5 mm cannula or even smaller—although the outer diameter of the shaft is not necessarily a limitation of the invention.

A suture assembly may include a suture, a force distribution member or anchor provided at a first end portion of the suture and an adjustable anchor or retainer provided at a second end portion or an intermediate portion of the suture spaced away from the force distribution member. The adjustable anchor may be moved along the suture toward the force distribution member to tighten the suture assembly and maintain the suture force distributing member in contact with a soft tissue repair prosthetic, such as a ventral patch, and/or the abdominal wall.

The suture assembly may be configured to permit movement of the adjustable anchor toward the force distribution member and prevent movement of the adjustable anchor away from the force distribution member to secure the anchor in one or more selected positions along the suture. For example, and without limitation, the suture may include barbs or barb-like features that cooperate with the suture anchor in a ratchet-like manner that allows relative movement between the suture anchor and the suture in only one direction.

The instrument may be configured to advance the suture anchor or retainer and at least a portion of the suture from within the abdominal cavity and across at least a portion of the abdominal wall to present the suture anchor or retainer on the opposite side of the fascia. The instrument may be adapted to present the suture anchor or retainer either above or below the skin surface for subsequent tightening of the suture assembly.

For procedures in which it is desired to advance and present the suture anchor or retainer above the skin surface, an anchor pusher may be provided for tightening the suture assembly. The anchor pusher may be configured to engage with and advance the suture anchor along the suture toward the force distribution member as the end of the suture above the skin surface is pulled outwardly to tension the suture. The anchor pusher may be configured to push and position the suture anchor below the skin surface, preferably adjacent the fascia.

Alternatively, an anchor pusher or anchor delivery device may be loaded with a separate suture anchor, or a component that cooperates with the suture anchor provided with the suture assembly, that is placed on the suture above the skin surface and then advanced along the suture to a position below the skin surface to tighten the suture assembly. For example, and without limitation, the anchor pusher may be loaded with an anchor that includes a ring and plug arrangement that is adapted to grip the suture when the plug is inserted into the ring with the suture located therebetween.

For penetration-free procedures in which it is desired to advance and position the suture anchor through the fascia and below the skin surface without penetrating the skin surface, the instrument may be configured to tighten the suture assembly. The instrument may be configured to control the penetration and delivery of the suture anchor to a desired location. The instrument may include a tensioning mechanism that is adapted to draw the suture through the suture anchor in either a proximal direction away from the skin surface and toward the force distribution member or a distal direction toward the skin surface and away from the force distribution member. As the suture is drawn through the suture anchor, the suture assembly is tightened by drawing the force distribution member and the anchor toward each other on opposite sides of the fascia.

The instrument may include a cutting mechanism that is adapted to sever excess suture when the suture assembly has been tightened. The instrument may also include an anchor ejector or ejection arrangement that is adapted to either facilitate or cause ejection of the suture anchor from the device.

The drive system may include a needle or other tissue piercing element with an end configured for piercing or penetrating tissue and/or a soft tissue repair prosthetic, such as a ventral hernia patch. The needle or tissue piercing element may be configured to carry the suture anchor across at least the fascia. The needle or tissue piercing element may be arranged to move in either one full stroke through the abdominal wall or in multiple partial strokes to control penetration through the abdominal wall. Alternatively, the drive system may include a drive element that is configured to drive the suture anchor, which may have a pointed tip for penetrating tissue, through and across the fascia.

The instrument may be configured as a reusable device, a disposable device, or a hybrid including a reusable aspect and a disposable aspect. Such a hybrid device might include, for example, a reusable handle and shaft and a disposable tip and suture assembly that is mountable to the shaft. A safety mechanism may be provided to prevent firing of the needle until the safety mechanism is released by a user. The instrument and suture assembly preferably will be sterilized prior to transfascial suturing.

Figure 2:
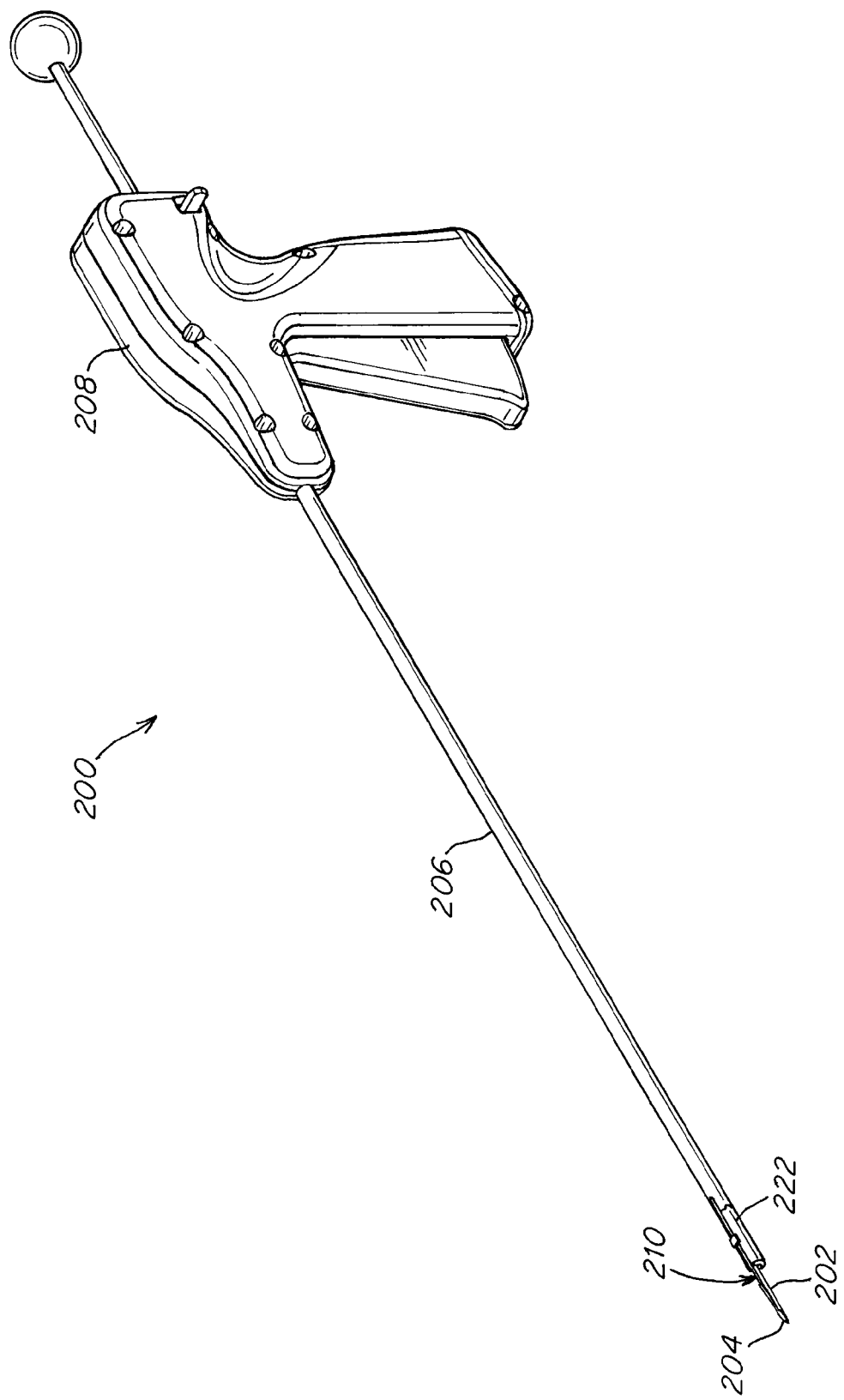
FIGS. 2-3 are illustrations of an instrument for transfascial delivery of a suture assembly.
Figure 3:
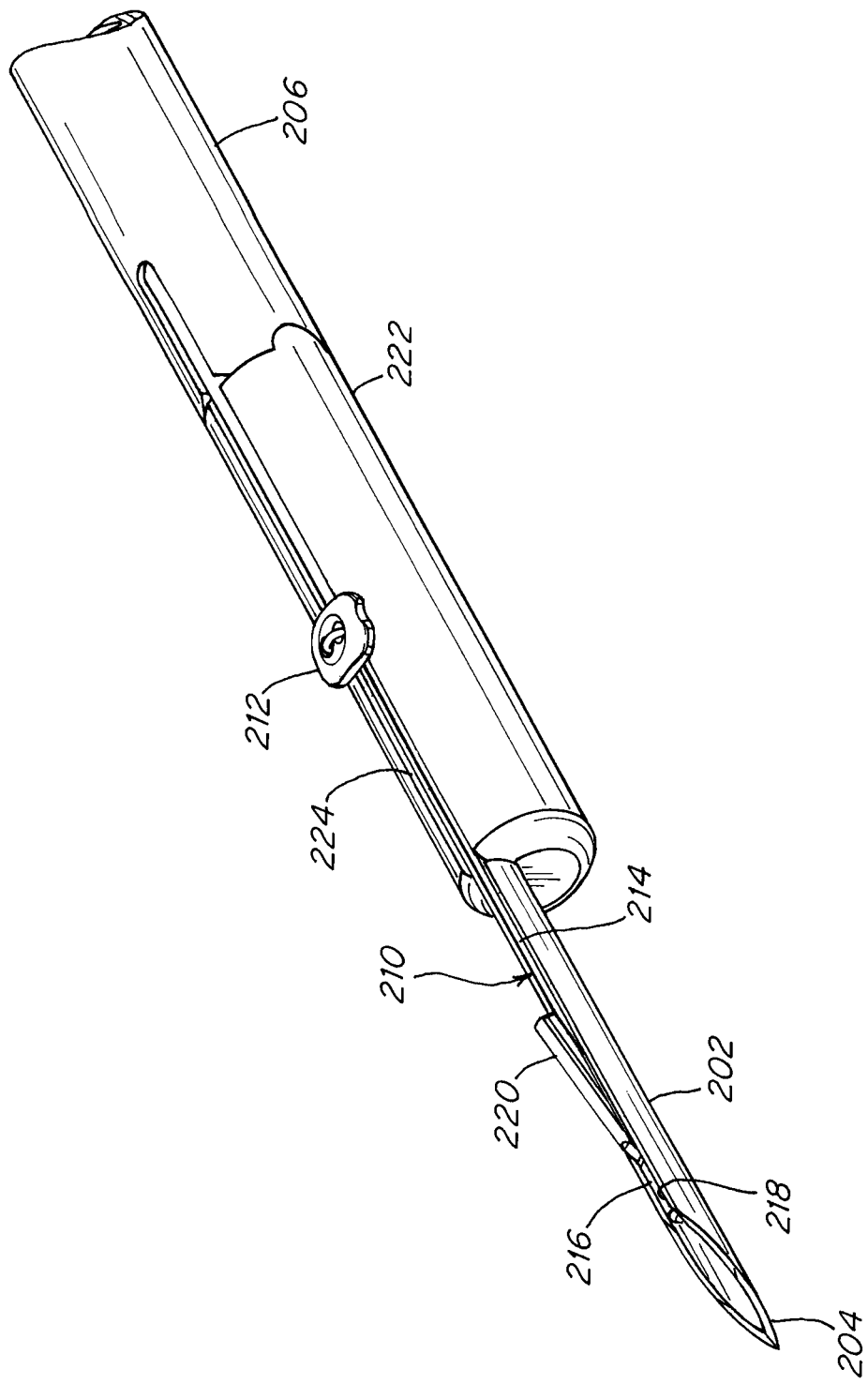

An instrument 200 for delivering a transfascial suture or suture assembly using an inside-out technique is shown in FIGS. 2-3. The instrument may be used within the abdominal cavity to deliver a suture through the abdominal wall. The instrument may include a needle 202, or other tissue penetrating element, with a distal end 204 adapted to pierce or penetrate a soft tissue repair prosthetic and abdominal wall tissue. If desired, the needle may employ a sharp end or a relatively blunt end adapted to pierce or penetrate the prosthetic and tissue. The needle may be housed within an elongated shaft 206 and may be operated with a needle drive mechanism included within and actuatable at a handle 208 provided at a proximal end of the shaft.

The instrument may be configured to deliver a transfascial suture assembly. In one illustrative embodiment shown in FIG. 4, the suture assembly 210 may include a force distribution member 212 located at an end portion of a suture 214 and a suture anchor or retainer 216 located along a portion of the suture 214 opposite the force distribution member. The force distribution member 212 may be configured to engage and hold an abdominal wall patch within the abdominal cavity against the abdominal wall. The suture anchor 216 may be adjustable along the suture 214 in a direction toward the force distribution member to tighten the suture assembly after the anchor is delivered with the instrument to a desired location outside the abdominal cavity.

The needle 202 may be hollow and adapted to receive and support the suture anchor or retainer 216 for delivery through the repair prosthetic and/or abdominal wall tissue. In one embodiment as shown in FIG. 3, the needle 202 may include a longitudinal slot 218 that extends in a proximal direction from the needle tip 204 and along a portion of the needle. The distal end of the slot 218 is open to receive a portion of a suture anchor 216, such as a toggle arm 220, when the anchor is loaded into the end of the needle. As shown, the slot 218 may be located along a portion of the needle opposite the penetrating tip. After deployment of the needle through the abdominal wall, the suture anchor 216 may be separated from the needle 202 by retracting the needle back through the abdominal wall causing the anchor to be drawn out of the needle. It is to be appreciated that the needle may employ other suitable configurations for accommodating a suture anchor as should be apparent to one of skill in the art.

As shown, the instrument 200 may include a tip 222 located at the distal end of the shaft 206. The tip 222 may be configured to close off the end of the shaft and support the needle 202 as it is extended from and retracted into the shaft. The tip 222 may include an elongated slot 224 with an open end that aligns with the needle slot 218 to accommodate the suture anchor 216 and suture 214 extending from the anchor. The tip 222 may also be configured to accommodate the force distribution member 212 of the suture assembly. For example, and without limitation, the tip may be provided with a relief, recess, slot or the like that is adapted to receive and support the force distribution member during delivery of the suture assembly with the instrument.

For some applications, the tip 222 may be configured as a disposable unit that is preloaded with a suture assembly 210 that can be attached to the shaft 206 to load a suture assembly to the instrument and released from the shaft after delivery of the suture assembly. In this manner, the needle 202, shaft 206 and handle 208 of the instrument may be a reusable unit that can be reloaded with disposable tips. The shaft 206 and tip 222 may employ a releasable interface, as should be apparent to one of skill in the art, for attaching and releasing the tip. For example, and without limitation, the interface may include a snap-fit arrangement. It is also to be appreciated that the tip may be permanently fixed to the shaft and the instrument can be reloaded, if desired, with one or more suture assemblies using other techniques as should be apparent to one of skill in the art.

Figure 4:
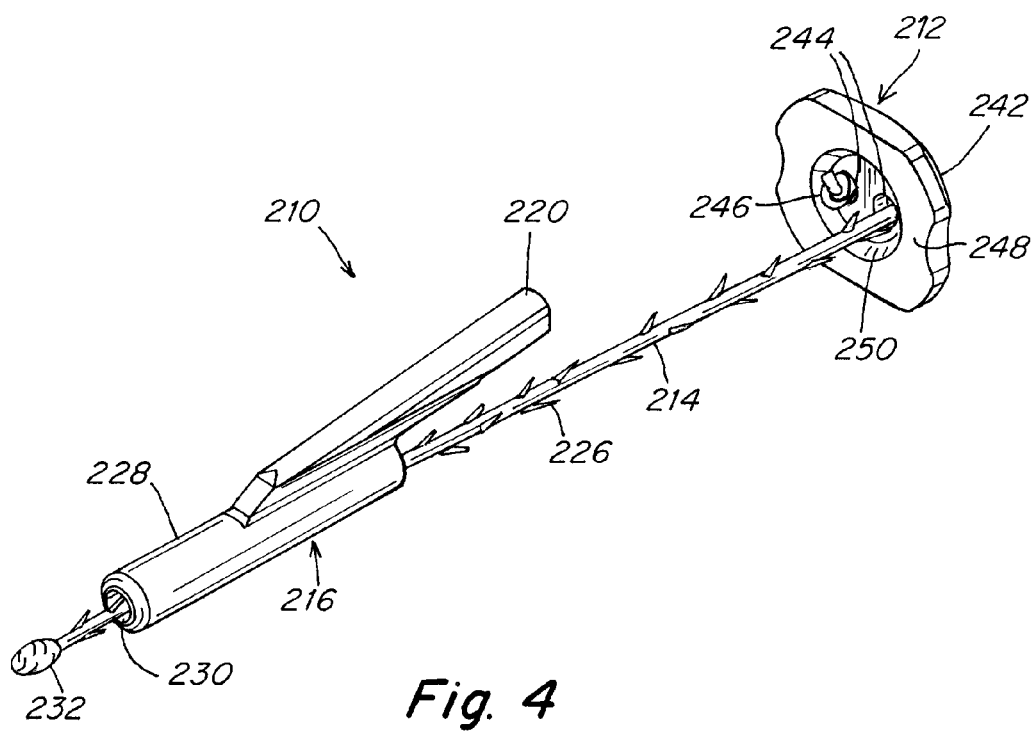
FIG. 4 is an illustration of a suture assembly for delivery by the instrument of FIGS. 2-3.

In one illustrative embodiment shown in FIG. 4, the suture assembly 210 may employ a ratchet-like arrangement that permits the suture anchor to move only in a direction toward the force distribution member. In one embodiment, the suture assembly may include a suture 214 having a plurality of barbs 226 or barb-like features spaced along at least a portion of its length that allow relative movement between the suture 214 and the anchor 216 in one direction while preventing relative movement therebetween in the opposite direction. The anchor 216 may be configured to coact with the barbed suture for tightening the suture assembly.

The suture anchor 216 may include a tubular body 228 with an axial throughbore 230 for receiving the suture 214 therethrough so that the location of the suture anchor is selectively variable relative to the suture. A toggle arm 220 may extend radially outward and in a generally axial direction beyond the proximal end of the body. The toggle arm may be configured to engage tissue or muscle and so as to prevent the anchor from being drawn back through the needle hole in the tissue and to help toggle or rotate the anchor 216 as the suture assembly is tightened. To prevent the suture from slipping out of the anchor body, an end 232 of the suture may be knotted, formed in a bulbous shape, or otherwise configured so as not to pass through the anchor.

Figure 5:
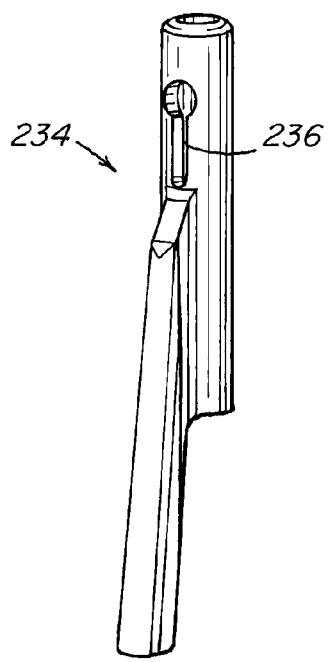
FIGS. 5-6 are illustrations of alternative suture anchors.
Figure 6:
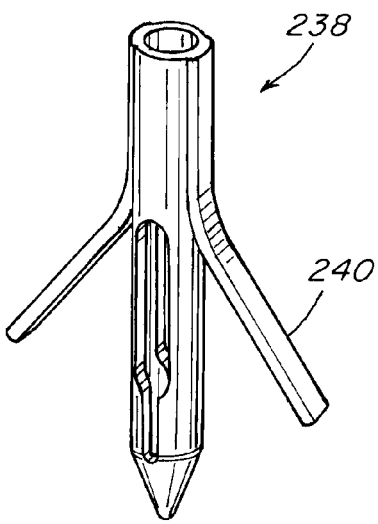

The suture anchor is not limited to the tubular shape with a toggle arm as shown and may have other configurations suitable for tightening and anchoring an end of the suture, as should be apparent to one of skill in the art. For example, and without limitation, a suture anchor 234 may include a suture cleat 236, as shown in FIG. 5, that is adapted to secure the anchor in a selected position along a smooth suture that is free of barbs or barb-like features by cinching the suture in the cleat. Alternatively, and again without limitation, a suture anchor 238 may be configured as an expansion anchor, as shown in FIG. 6, that includes one or more expandable members 240 that expand outwardly from a collapsed position suitable for delivery through the abdominal wall to an expanded configuration, as shown, upon deployment.

As shown in FIG. 4, the force distribution member 212 may include a body 242 with a substantially plate-like or planar configuration suitable for spreading forces applied along the suture when the suture assembly is tightened against a repair patch or the abdominal wall. The plate-like or planar arrangement may have any suitable configuration including, without limitation, rectangular, square, circular, oval, triangular, flat, slightly convex, slightly concave, and hybrids of the foregoing.

The force distributing member is not limited to the plate-like shape shown, as should be apparent to one of skill in the art, and may have other configurations such as a tubular configuration or T-bar arrangement. Other three-dimensional and substantially planar shapes, as well as compound shapes including three-dimensional and planar aspects, are contemplated as one of skill in the art will appreciate. Further, one or more surfaces of the force distributing member may be adapted for contact or engagement with the soft tissue repair prosthetic. For example, a force distributing member may include one or more specially shaped surfaces, or facets, which may be planar, convex, concave, or other arrangement suitable to promote contact or engagement between the force distributing member and the soft tissue repair prosthetic.

The force distribution member 212 may be attached to an end of the suture by threading an end portion of the suture through a pair of holes 244. To prevent the suture from slipping out of the anchor body, an end 246 of the suture may be knotted, formed in a bulbous shape, or otherwise configured so as not to pass through the force distribution member. As shown in FIG. 4, a side 248 of the force distribution member that is adapted to face and engage a repair prosthetic of the abdominal wall may be provided with a recess 250 or similar feature that is adapted to receive the formed end of the suture therein below the abdominal wall facing side 248.

The force distributing member may be attached to the suture using other suitable arrangements as should be apparent to one of skill in the art. For example, and without limitation, the force distributing member may be joined to the suture through mechanical arrangements, such as by crimping the force distributing member to the suture or by one or more clamps or wedges provided in the force distributing member that may be engaged to the suture. Alternatively, and again without limitation, the force distributing member may be joined by thermal or chemical bonding with the suture, by heat shrinking the force distributing member to the suture, or by an adhesive applied between the two components. Further, the force distributing member may be integrally formed with the suture, such as by hardening or reshaping a portion of the suture.

An illustrative method of delivering a transfascial suture using the instrument 200 of FIGS. 2-3 will be described in connection with FIGS. 7-12.

Figure 7:
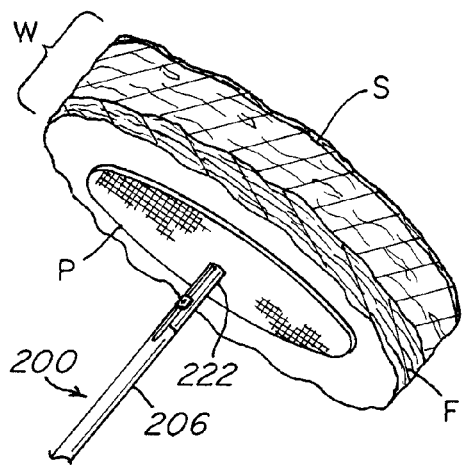
FIGS. 7-12 illustrate a method of transfascial suturing using the instrument and suture assembly of FIGS. 2-4.

The instrument 200 may be inserted into the abdominal cavity in a sharps-free condition with the needle 202 retracted within the shaft 206. As shown in FIG. 7, following placement of the instrument within the abdominal cavity at a desired location against the abdominal wall patch P and/or abdominal wall W, the needle 202 is extended from the distal end of the shaft 206 with the needle tip exposed to penetrate the abdominal wall W and the skin surface S. In one embodiment, the needle may be extended from the shaft with a drive mechanism provided in the handle that employs a multi-stage and/or partial stroke actuation. For example, and without limitation, the drive mechanism may be adapted to extend the needle in partial strokes to incrementally penetrate the abdominal wall with each successive actuation. The drive mechanism continues to be actuated until the needle 202 either exits the skin or produces skin tenting. If desired, actuation of the device may be paused, either when skin tenting is observed or to otherwise perform palpation of the abdominal wall, so that the surgeon may make a skin incision prior to needle penetration, thereby lowering the force that may be necessary for the needle to penetrate the skin.

Figure 8:
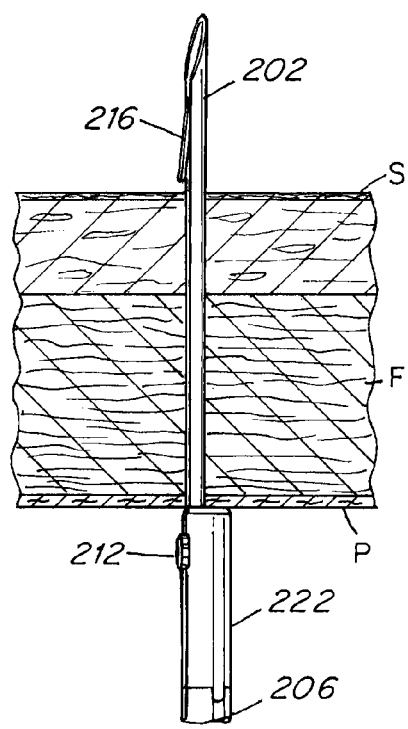

As shown in FIG. 8, actuation of the drive mechanism continues until the needle 202 is fully extended through the abdominal wall and skin to present the suture anchor 216 outside the abdominal cavity and above the skin surface S. The needle may then be retracted into the shaft causing the suture anchor 216 to engage the skin surface and separate from the needle. Following retraction of the needle, the distal end of the instrument 200 may be pulled into the abdominal cavity and away from the patch P and abdominal wall W to separate the suture assembly 210 from the instrument.

Figure 9:
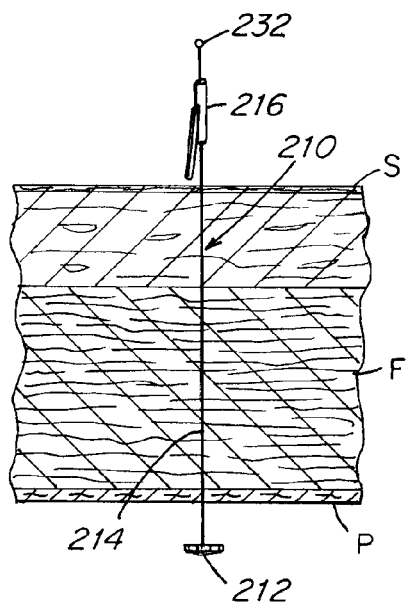

As shown in FIG. 9, the suture 214 extends through the patch P and abdominal wall W with the force distribution member 212 located within the abdominal cavity adjacent the patch P and the suture anchor 216 located outside the abdominal cavity above the skin surface S.

Figure 10:
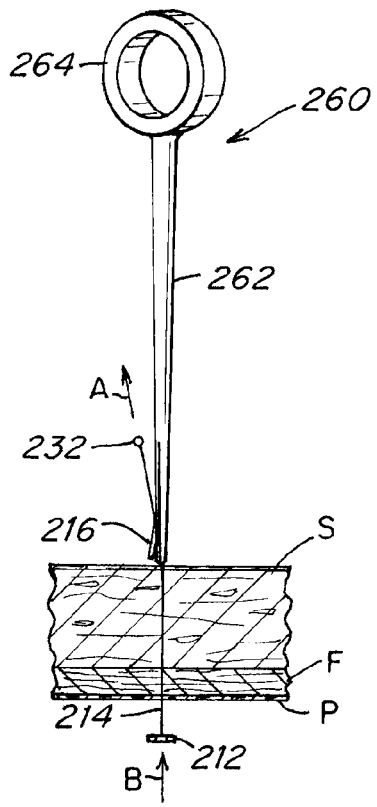

As shown in FIG. 10, an anchor pusher 260 may be coupled to the suture anchor 216 outside the patient's body. The end 232 of the suture extending outside the body may be pulled (arrow A) outwardly away from the abdominal cavity to draw (arrow B) the force distribution member 212 against the patch and abdominal wall and tension the suture. While pulling the suture 214, the suture anchor 216 may be advanced (arrow C) along the suture and into the needle hole formed through the skin layer using the anchor pusher 260.

Figure 11:
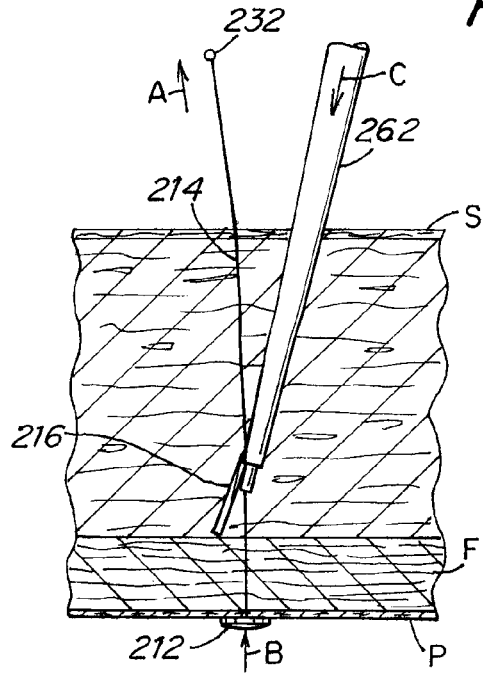

As shown in FIG. 11, advancement of the anchor 216 continues until the anchor is positioned below the skin surface S and the suture assembly is tightened to secure the patch against the wall. As shown, the suture anchor 216 may be advanced through the skin layer to engage the fascia F.

Figure 12:
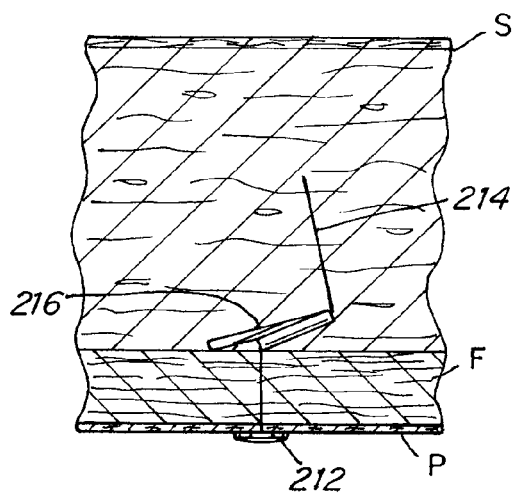

As shown in FIG. 12, with the suture assembly sufficiently tightened, the anchor pusher 260 is removed and excess suture may be trimmed below the skin surface S in a manner that should be apparent to one of skill in the art.

The above described method may be repeated to provide additional suture fixation points through the abdominal wall patch and/or fascia as desired by the surgeon for carrying out the particular repair procedure.

Figure 13:
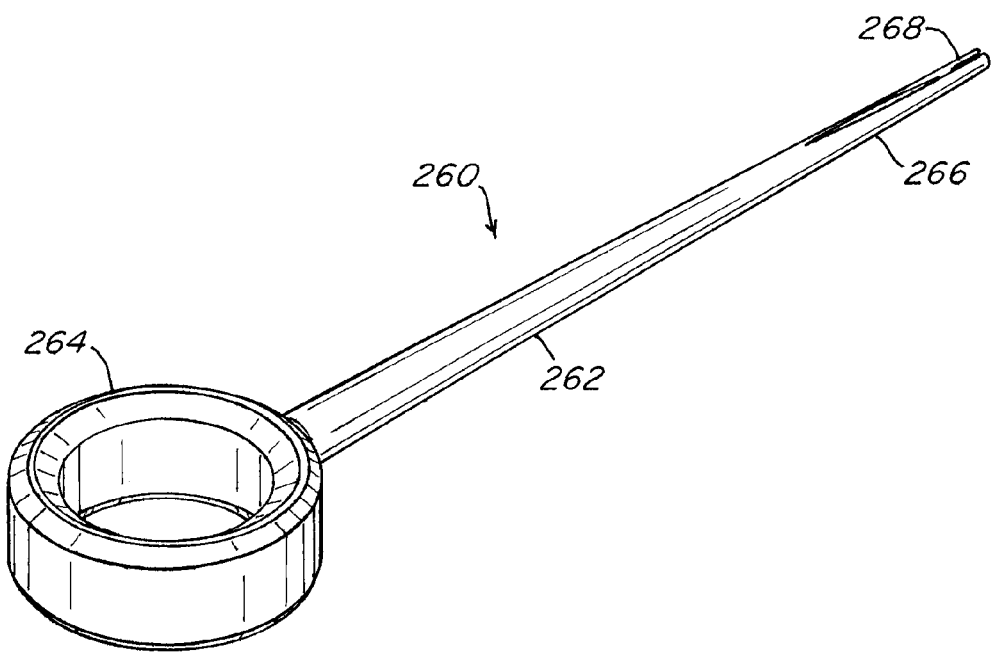
FIG. 13 is an illustration of an anchor pusher for use with the method of FIGS. 7-12 for tightening the suture assembly of FIG. 4.

In one illustrative embodiment shown in FIG. 13, the anchor pusher 260 may include an elongated body 262 with a handle 264 at a proximal end of the body. The distal portion 266 of the body may be configured to couple with the suture anchor 216. In one embodiment, the distal portion of the pusher body may be hollow or otherwise be provided with a receptacle adapted to receive at least a portion of the suture anchor therein. As shown, the pusher body 262 may include a longitudinal slot 268 that extends in a proximal direction from the distal tip and along a portion of the body. The distal end of the slot 268 is open to receive a portion of the suture anchor 216, such as the toggle arm 220, and accommodate the suture when the anchor is attached to the pusher. As shown, the pusher body 262 may taper downwardly in a direction from the handle 264 toward the distal tip to facilitate insertion of the pusher body through tissue. It is to be appreciated that the anchor pusher may employ other suitable configurations for accommodating and advancing a suture anchor as should be apparent to one of skill in the art.

Figure 14:
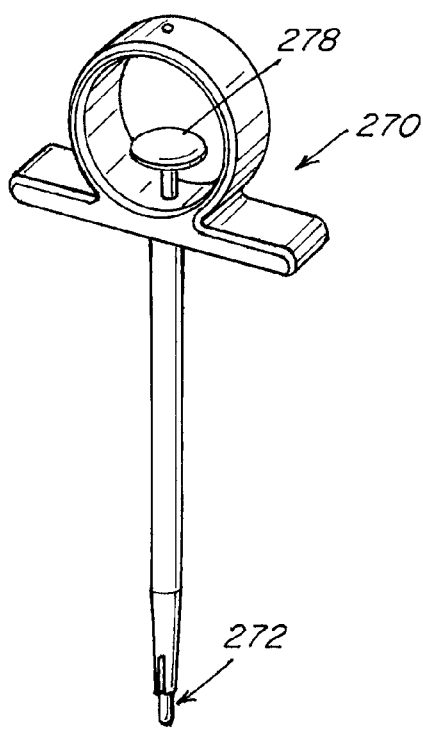
FIGS. 14-15 are illustrations of a suture anchor delivery device and a suture anchor that may be secured to a suture with the device.
Figure 15:
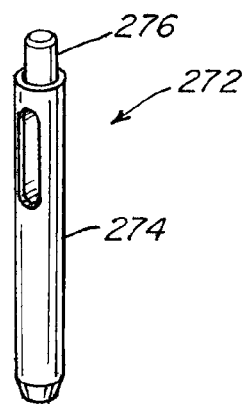

For some applications, it may be desirable to deliver a separate suture anchor, or a component that cooperates with a suture anchor provided with the suture assembly, after the suture has been delivered through the abdominal wall. As shown in FIGS. 14-15, an anchor delivery device 270 may include an elongated body that may be loaded with a suture anchor 272, or a component that cooperates with the suture anchor provided with the suture assembly, that is placed on the portion of the suture extending above the skin surface and then advanced along the suture to a position below the skin surface to tighten the suture assembly. As shown in FIG. 15, the suture anchor 272 may include a ring 274 and plug 276 arrangement that is adapted to grip the suture when the plug 276 is inserted into the ring 274 with the suture located therebetween. The pusher or delivery device may include a plunger 278, or other arrangement, that may be actuated at the device handle to drive the plug into the ring to secure the anchor at a selected position along the suture.

Figure 16:
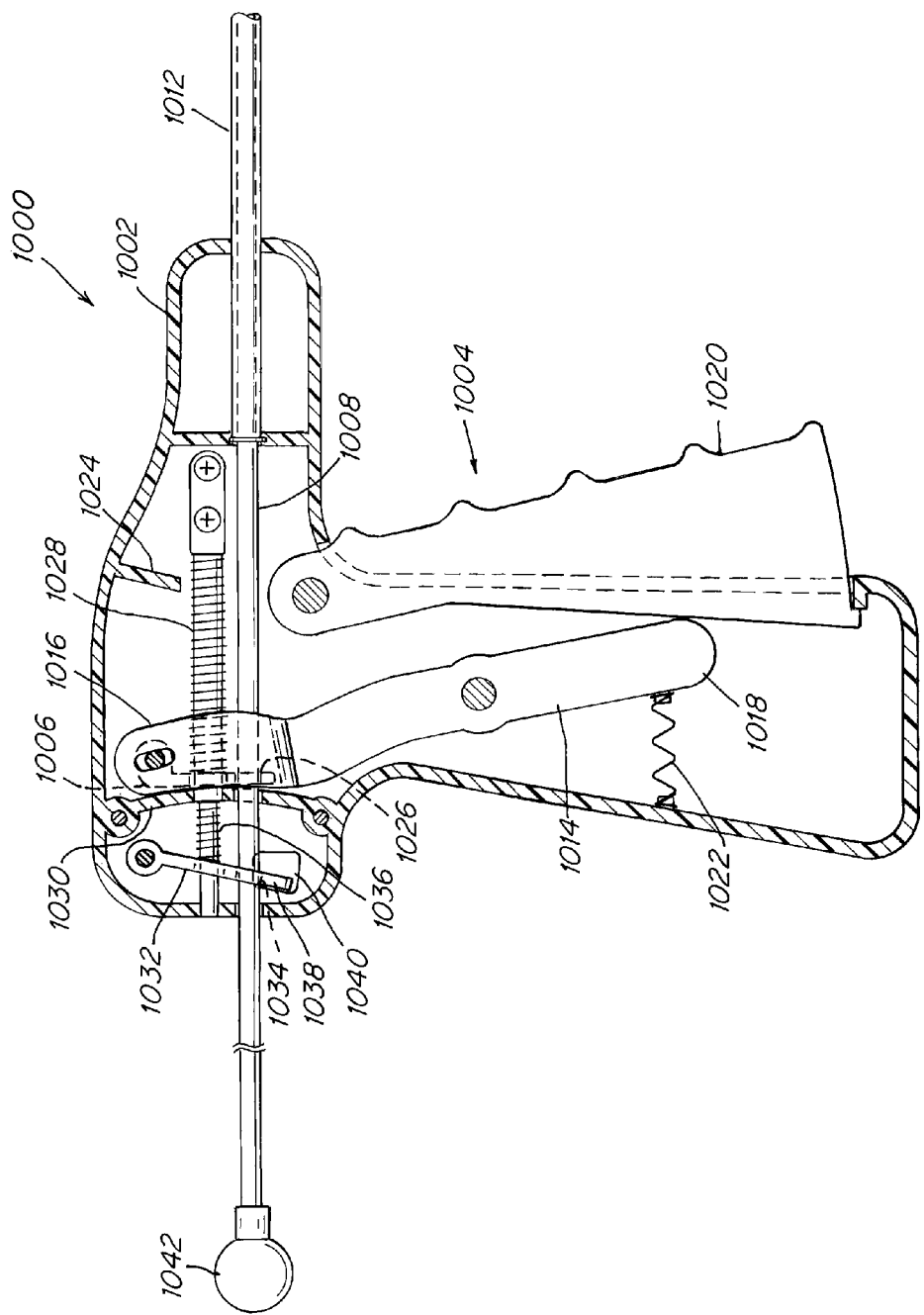
FIGS. 16-17E are partial sectional illustrations of a drive mechanism for the instrument of FIGS. 2-3 for transfascial delivery of a suture assembly.
Figure 17A:
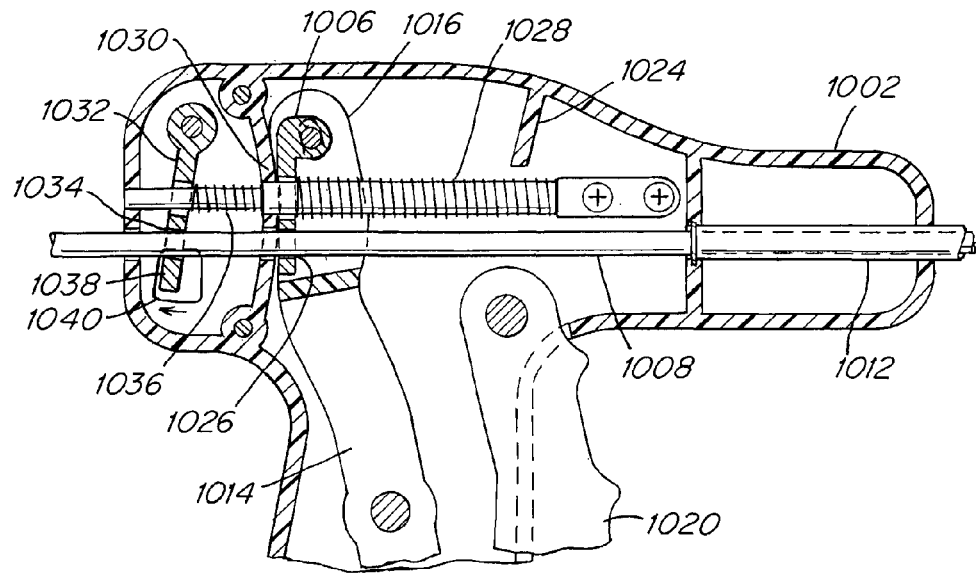
Figure 17B:
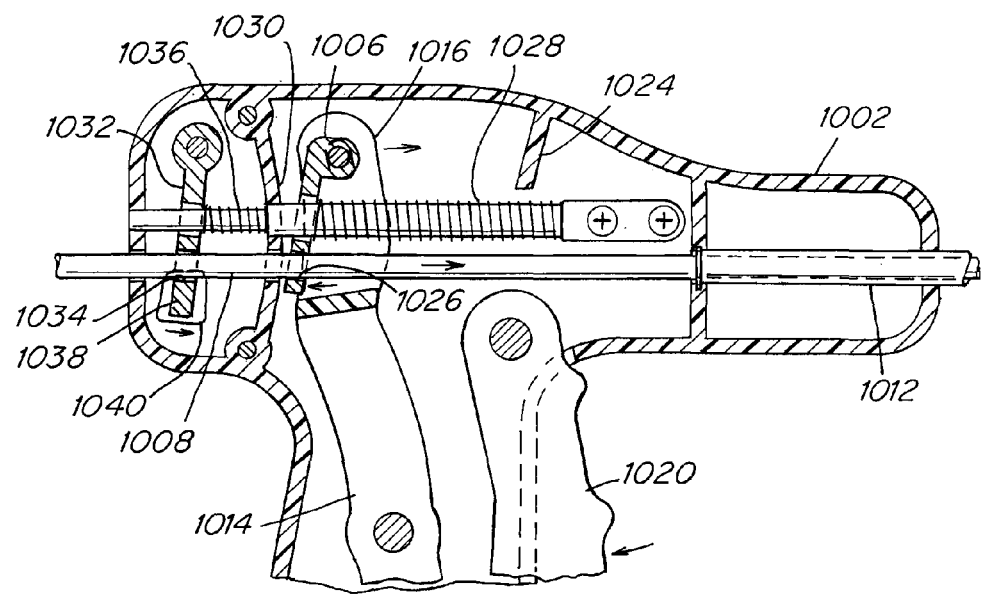
Figure 17C:
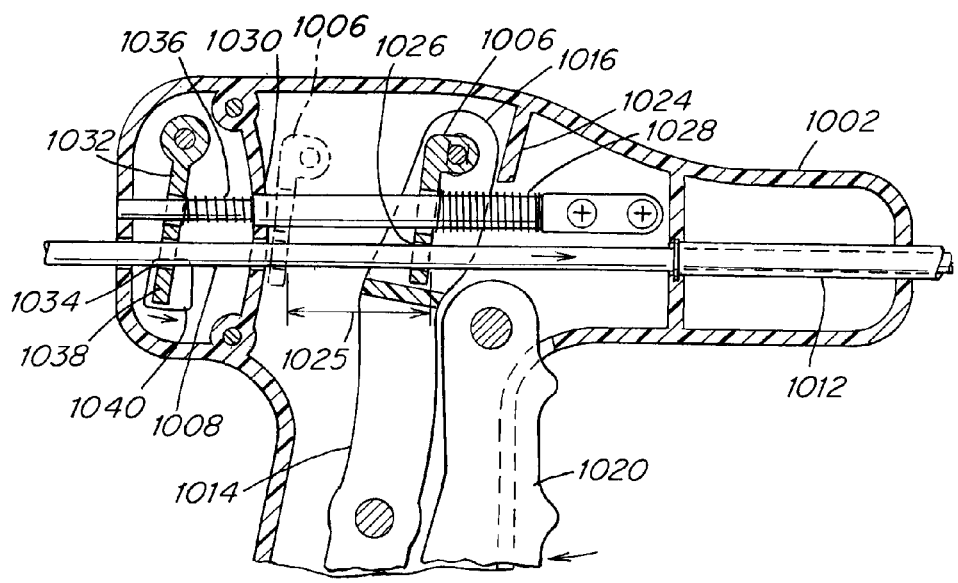
Figure 17D:
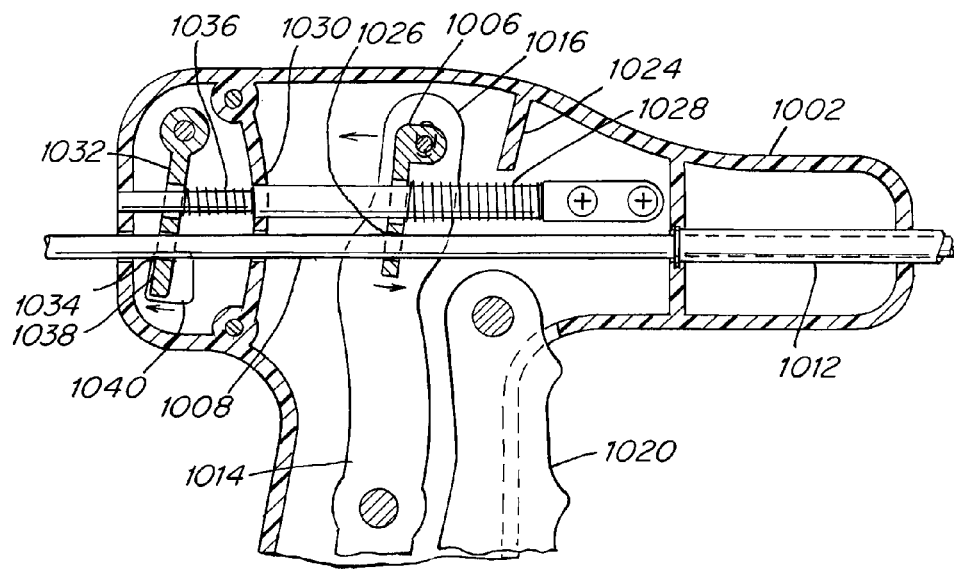
Figure 17E:
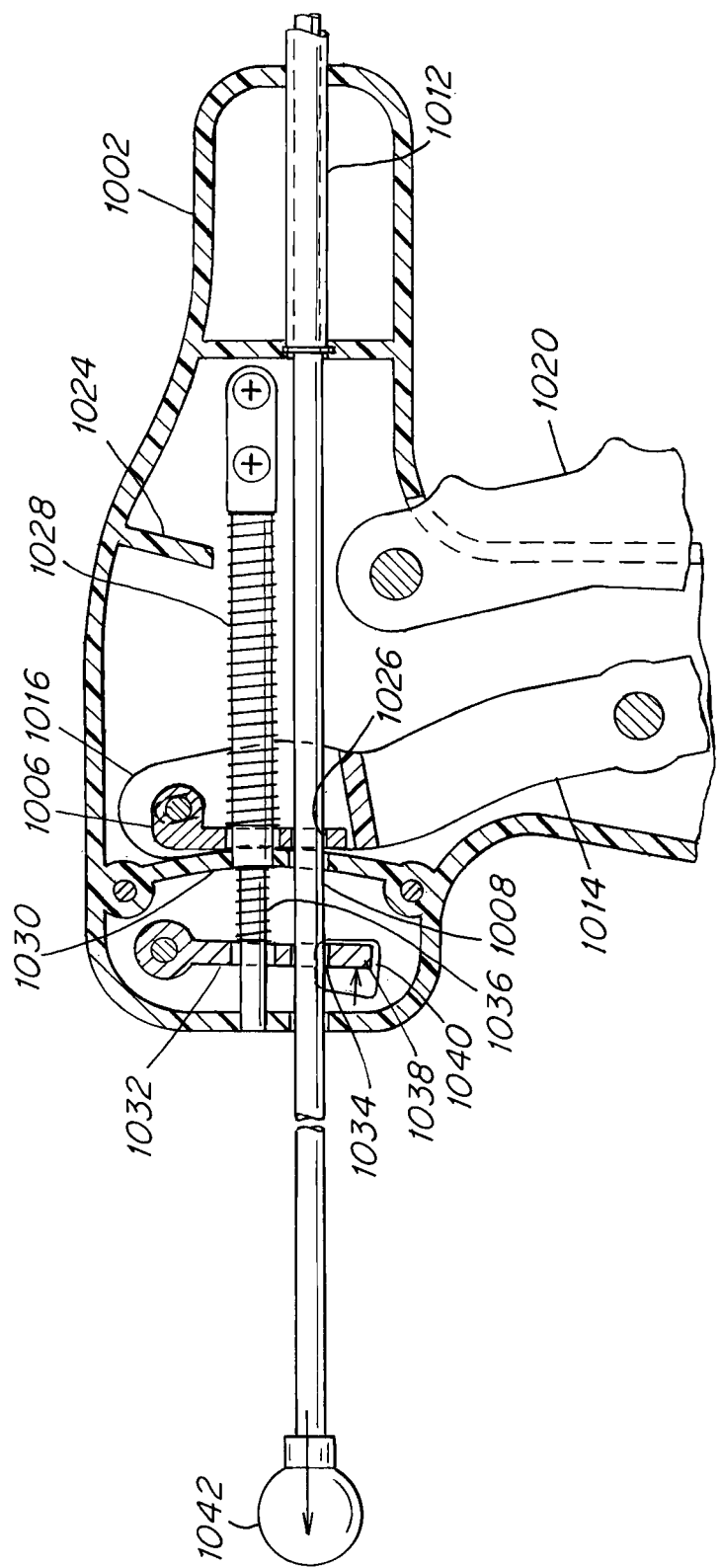
Figure 18:
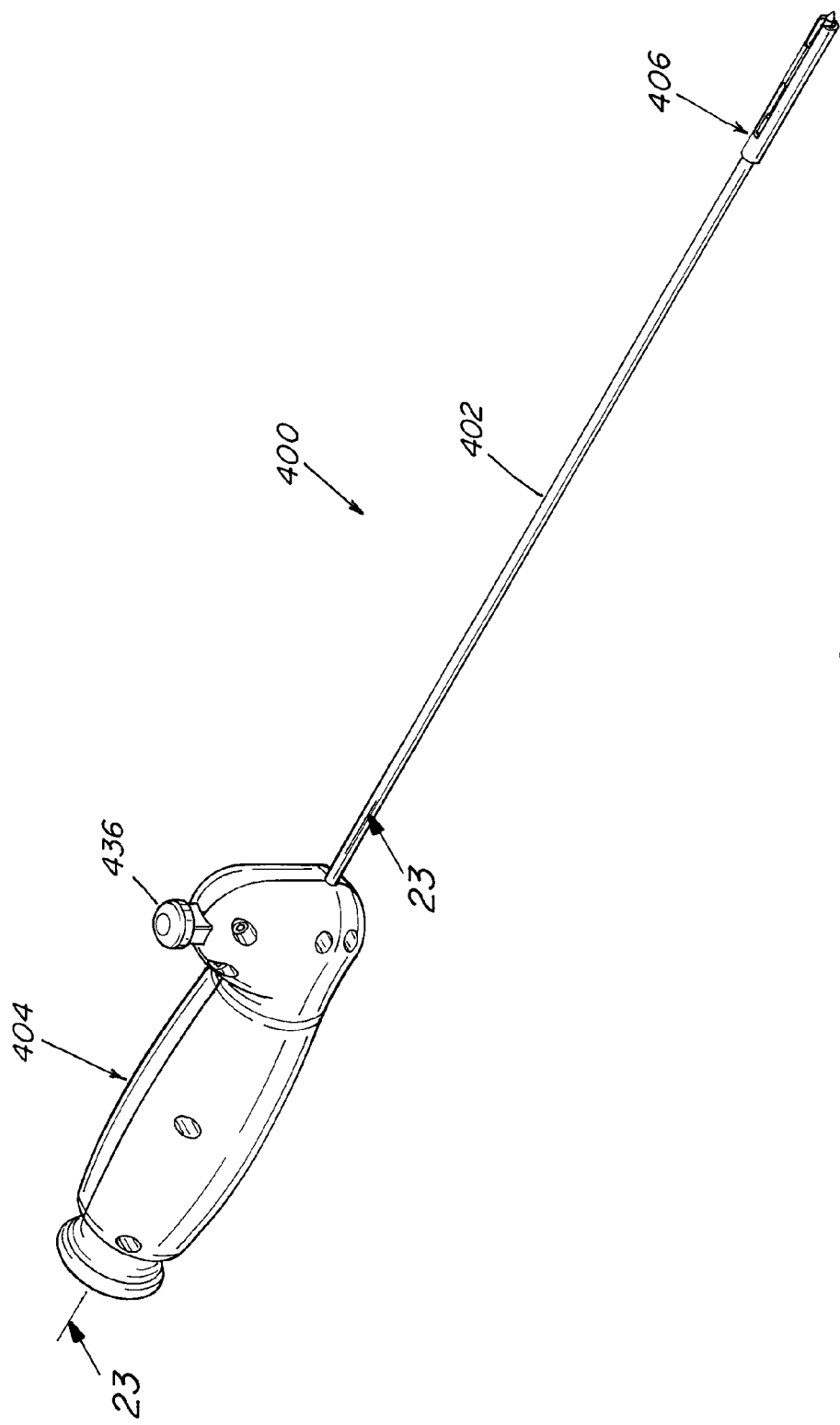

In one illustrative embodiment shown in FIGS. 16-17E, a system 1000 for actuating the needle or other tissue piercing element of a delivery instrument, such as shown in FIGS. 2-3, includes a handle body 1002 which supports a drive mechanism adapted to actuate the needle or other tissue piercing element in one or more partial strokes. The drive mechanism 1004 may include an advancer 1006 that is adapted to releasably engage a proximal portion 1008 of a needle, a needle drive shaft coupled to a needle or other tissue piercing element upon actuation of the drive mechanism to advance the needle in a distal direction relative to an outer shaft 1012, which may correspond to the shaft 206 of the instrument 200. An actuation lever 1014 is mounted for pivotal movement and includes an upper end 1016 coupled to the advancer and a lower end 1018 operatively engaged with a trigger 1020. As shown, the upper end of the trigger is mounted for pivotal movement with the lower portion of the trigger operatively engaged with the lever.

As shown in FIG. 16, the trigger 1020 may be pivoted against the biasing force of a spring 1022, such as a compression or torsion spring, acting upon the lower end 1018 of the lever causing the lever to pivot about its axis with the upper end 1016 of the lever moving in the distal direction. The advancer 1006 is pivotally mounted to the actuation lever and is similarly advanced in the distal direction to drive the needle distally from the shaft. A first stop 1024 may be provided to engage and limit the distal travel of the upper end of the lever corresponding to the desired amount of needle stroke 1025 per actuation, as shown in FIG. 17C.

The advancer 1006 is adapted to engage the proximal portion 1008 of the needle or needle drive shaft when the drive mechanism is actuated to advance the needle and to release the needle or needle drive shaft and slide along the proximal portion of the needle or drive shaft when the trigger is released and returns to its initial position under the biasing force of the spring 1022, as shown in FIG. 17D. In one embodiment, the advancer 1006 includes an advance lever configured with a clutch-like arrangement in which the advance lever is adapted to pivot in the proximal direction to grip and advance the needle or needle drive shaft when the advancer is moved in the distal direction by the actuation lever, as shown in FIGS. 17B-17C. The advance lever pivots in the opposite or distal direction to release and slide along the needle or drive shaft in the proximal direction to reset its position along the needle or drive shaft for a subsequent actuation.

In one embodiment, the advance lever includes an opening 1026 at its lower end that receives the needle or needle drive shaft and is configured to engage or release the needle or drive shaft in response to the angular position of the advance lever as it pivots relative to the needle or drive shaft. As shown in FIGS. 17B-17C, the advance lever pivots against the biasing force of a spring 1028, such as a compression spring, to engage the needle or drive shaft as the advancer is moved distally during actuation of the lever. A second stop 1030 is provided to abut and hold the advancer out of engagement with the needle or drive shaft prior to actuation or upon reset of the drive mechanism.

The drive mechanism may include a lock 1032 to engage and hold the needle or needle drive shaft in an extended position following each actuation of the device. As shown, the lock is located proximal to the advancer and is adapted to engage and prevent proximal movement of the needle or drive shaft to reduce inadvertent retraction of the needle from its desired position during a suturing procedure.

In one embodiment, the lock 1032 may include a locking lever configured with a clutch-like arrangement in which the locking lever is pivotally mounted between a locked position (FIG. 17A) to prevent proximal retraction of the needle and a release position (FIG. 17E) to permit proximal retraction. The locking lever includes an opening 1034 at its lower end, similar to the locking lever, that receives the needle or needle drive shaft and is configured to engage or release the needle or drive shaft in response to the angular position of the locking lever as it pivots relative to the needle or drive shaft. The locking lever may be biased to the locked position with a spring 1036, such as a compression spring, located between the second stop 1030 and the lock which applies a biasing force that pivots the locking lever in a proximal direction, as shown in FIG. 17A. Distal movement of the needle or needle drive shaft in response to actuation of the advancer 1006 causes the locking lever 1032 to pivot slightly in the distal direction permitting the needle or drive shaft to be drawn through the lock, as shown in FIGS. 17B-17C. Upon completion of the actuation stroke, the lock 1032 returns to the locked position, as shown in FIG. 17D, to hold the needle in the extended position as the advancer 1006 resets for the next actuation.

As shown in FIG. 17E, the lock 1032 may be released by a user to permit retraction of the needle by manually pushing and pivoting the locking lever in the distal direction against the biasing force of the spring 1036. The lock may be released by pressing against one or more laterally extending tabs 1038 extending from the lower end of the locking lever and through an access opening 1040 in the handle body. The access opening 1040 may be configured to engage the tabs and limit the pivoting of the locking lever. As shown, a knob 1042 may be located at the proximal end of the needle for gripping and retracting the needle, after releasing the lock, to reset the instrument following delivery of a suture.

In one embodiment, a drive mechanism for providing partial needle advancement may be configured to advance the needle in partial strokes of approximately 1.0 inch increments in response to each actuation of the trigger. An instrument employing such a mechanism may be configured to provide a total needle stroke of approximately 4.0 inches. If desired, the drive mechanism may be configured to provide an initial stroke of approximately 0.2 inches to slightly expose the needle tip for positioning the instrument against a patch and/or the abdominal wall. However, it is to be appreciated that the drive mechanism may be configured to provide any amount of partial or incremental needle stroke and the instrument may be configured to provide any amount of total needle stroke as should be apparent to one of skill in the art.

Having described one embodiment of a system for actuating a needle or other tissue piercing element of a delivery instrument, it is to be appreciated that other drive mechanisms are contemplated for actuating a delivery instrument with one or more partial strokes as should be apparent to one of skill in the art. For example, and without limitation, the drive mechanism may include a gear drive, a rack and pinion drive or other suitable drives.

For some transfascial suturing procedures, it may be desirable to employ a transfascial suture assembly with a suture anchor or retainer that may be deployed and/or implanted below the skin surface, for example, between the fascia and the dermal layer without penetrating the skin surface. The suture assembly may be configured to be tightened subdermally using a knotless procedure.

An instrument 400 for subdermal delivery of a transfascial suture or suture assembly using an inside-out technique is shown in FIGS. 18-23. The instrument may be used within the abdominal cavity to deliver a suture or suture assembly through at least a portion of the abdominal wall and to tighten the suture or suture assembly from within the abdominal cavity without penetrating the skin surface of the patient.

The instrument may include a drive system for delivering at least a portion of a suture assembly through a soft tissue repair prosthetic and/or abdominal wall tissue. The drive system may be housed within an elongated shaft 402 and may be operated with a drive mechanism included within and actuatable at a handle 404 provided at a proximal end of the shaft. The instrument may include a tip 406 located at the distal end of the shaft 402 that is adapted to support a suture assembly thereon for delivery with the drive system.

Figure 24:
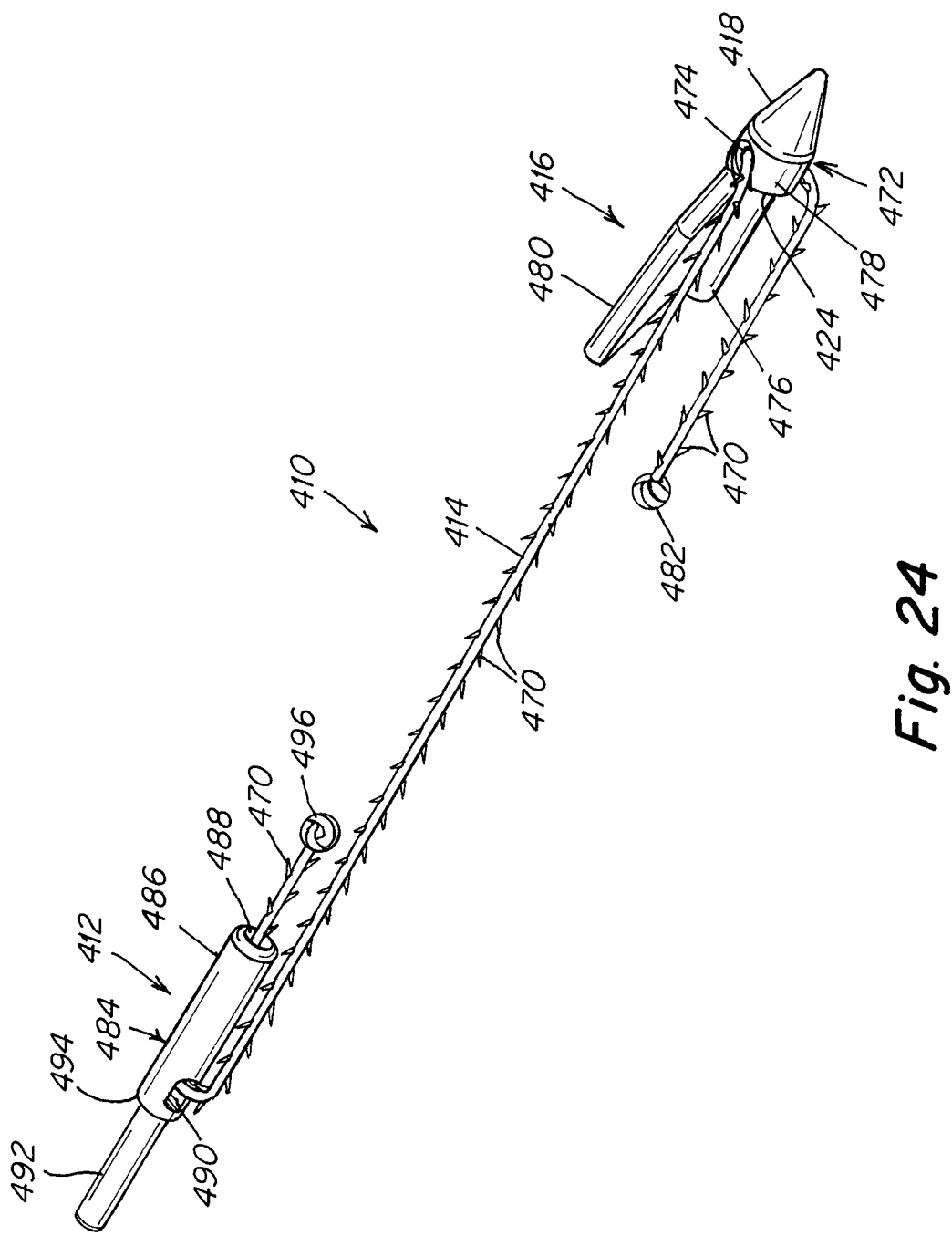
FIG. 24 is an illustration of a suture assembly for delivery by the instrument of FIGS. 18-23.

In one illustrative embodiment shown in FIG. 24, the suture assembly 410 may include a force distribution member 412 located at an end portion of a suture 414 and a suture anchor or retainer 416 located along a portion of the suture 414 opposite the force distribution member. The force distribution member 412 may be configured to engage and hold an abdominal wall patch within the abdominal cavity against the abdominal wall. The suture anchor 416 may be adjustable along the suture 414 in a direction toward the force distribution member to tighten the suture assembly after the anchor is delivered with the instrument to a desired location outside the abdominal cavity. As shown, the suture anchor may include a pointed distal tip 418 that is adapted to penetrate a soft tissue repair prosthetic and/or abdominal wall tissue as the anchor is pushed therethrough with the drive system.

Figure 22:
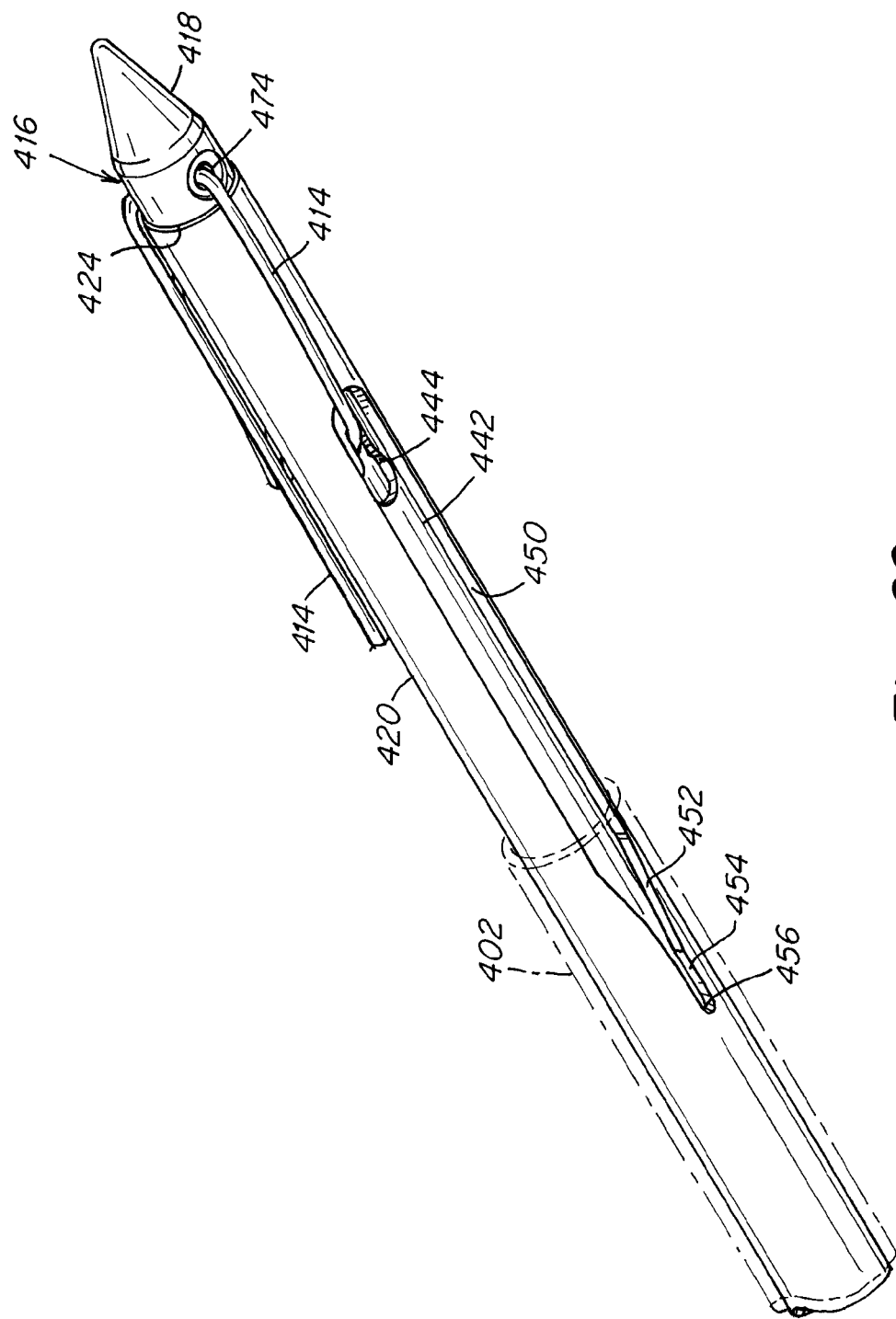

In one embodiment as shown in FIGS. 20-22, the drive system may include a drive element 420, such as an elongated tube, that extends within the shaft 402 and supports a suture anchor 416 loaded at a distal end of the instrument. The drive element 420 may extend through and be connected to the handle 404 to fix the drive element in a stationary position relative to the handle. As described further below, the drive element is adapted to drive the suture anchor through the soft tissue repair prosthetic and/or abdominal wall tissue by pushing the instrument in a distal direction with the handle.

Figure 19:
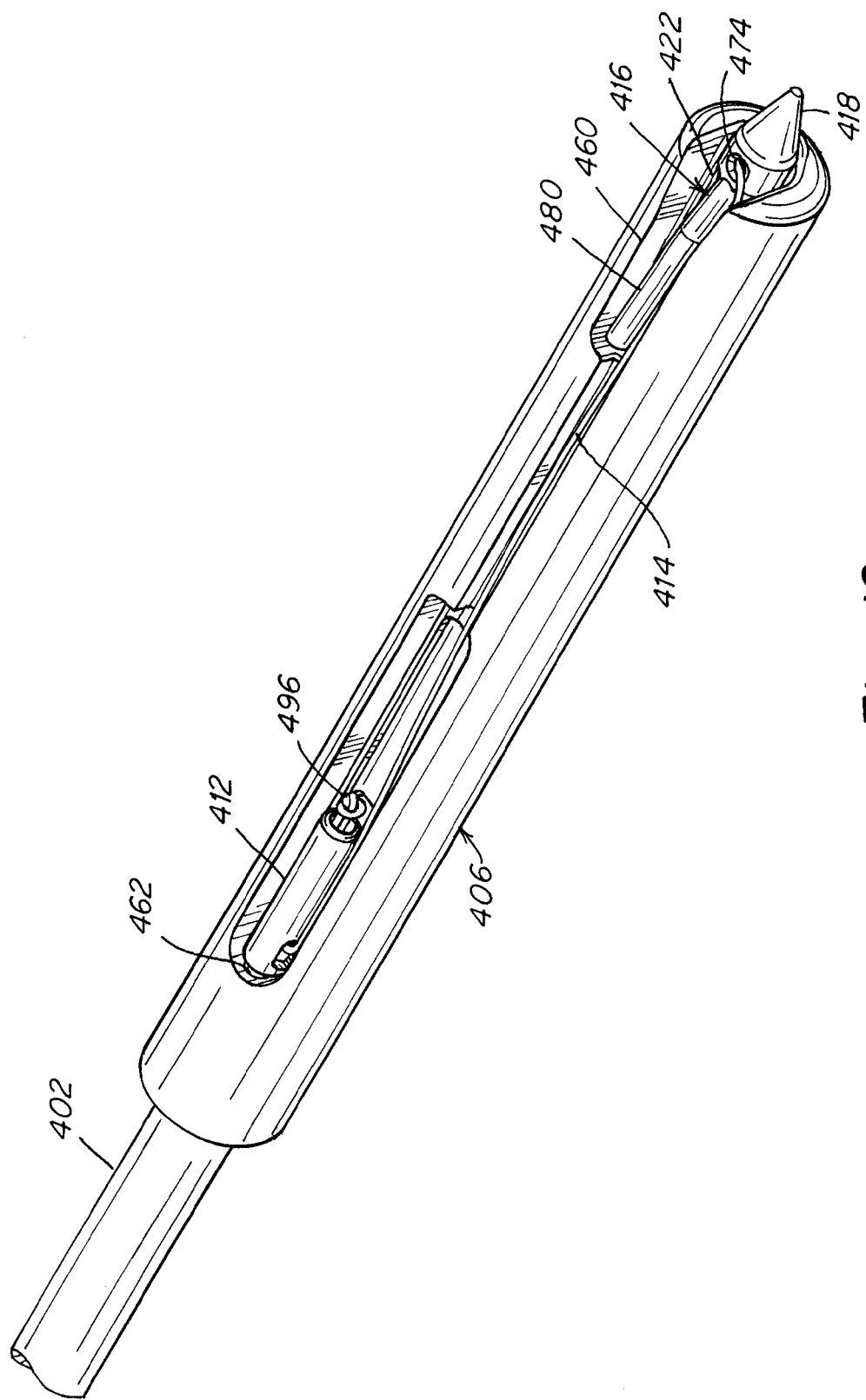

The drive element may include a hollow tube adapted to receive and support the suture anchor or retainer for delivery through the repair prosthetic and/or abdominal wall tissue. As shown in FIGS. 19-20, the drive tube 420 may include a longitudinal slot 422 that extends in a proximal direction from the distal end and along a portion of the tube. The distal end of the slot is open to receive a portion of a suture anchor, such as a toggle arm, when the anchor 416 is loaded into the end of the tube. The distal end of the tube may engage a shoulder 424 that may be provided on the suture anchor for exerting a force on the anchor to drive the anchor through the repair prosthetic and/or abdominal wall tissue. After deployment of the suture anchor 416 or retainer the abdominal wall, the suture anchor or retainer may be separated from the drive element 420 by retracting the drive tube back through the abdominal wall to thereby cause the anchor to dislodge from the tube. It is to be appreciated that the drive element may employ other suitable configurations for accommodating a suture anchor as should be apparent to one of skill in the art.

The shaft 402 is retractable in a proximal direction over the drive element 420 to expose the distal end or tip of the suture anchor. The shaft 402 may be biased in the distal direction to enclose at least a portion of the suture anchor for insertion and manipulation within the abdominal cavity. As shown, a portion of the suture anchor tip may protrude from the distal end of the shaft, when the shaft is fully extended, to facilitate positioning of the instrument at a desired location within the abdominal cavity. If desired, the shaft may be configured to extend further to enclose the tip of the suture anchor.

Figure 23:
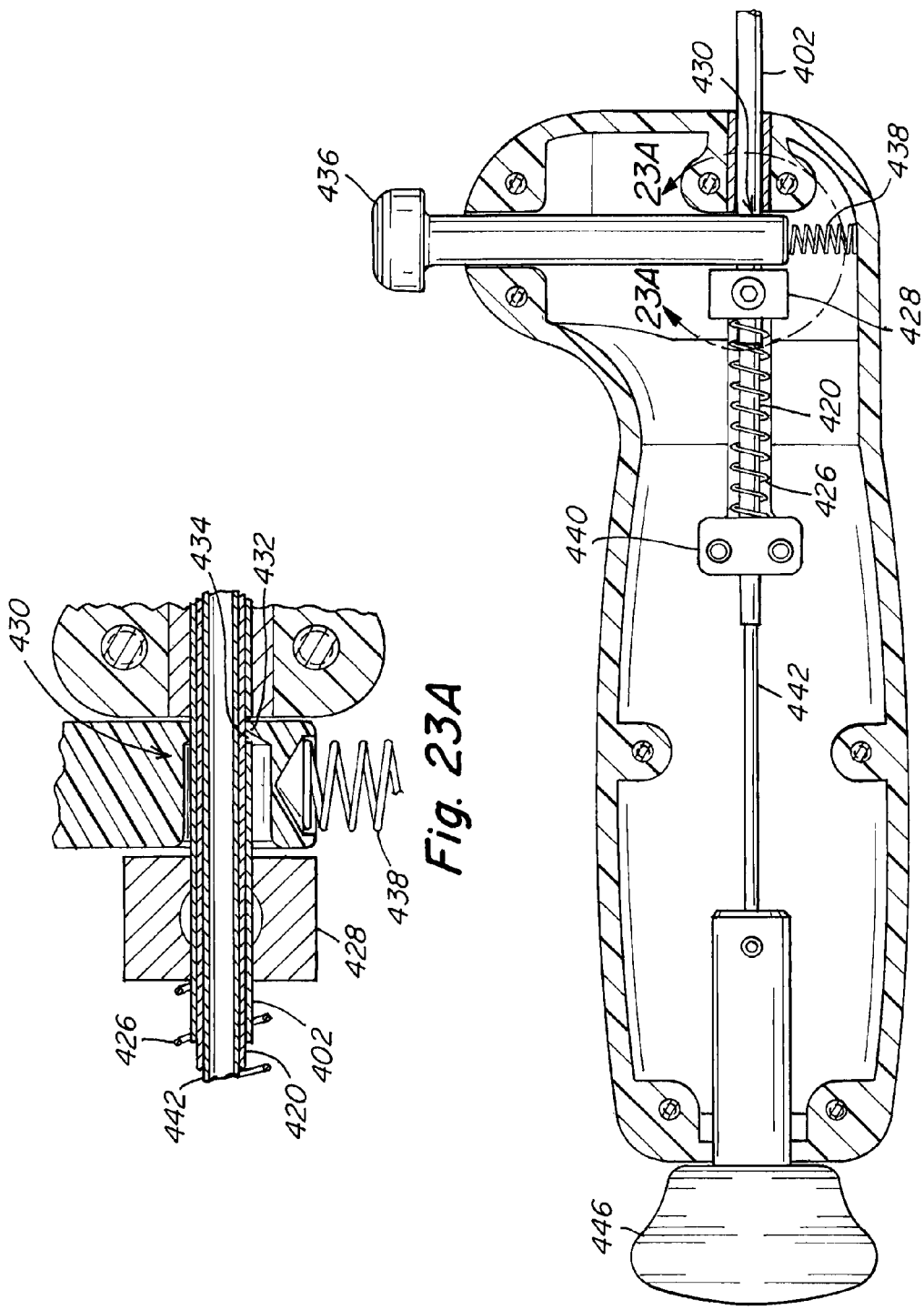

As shown in FIG. 23, a spring 426, such as a compression spring, may be located about a proximal portion of the drive tube 420 and coupled to the proximal end of the shaft 402 with a coupler 428 that is movable along the proximal portion of the drive tube. With the distal end of the shaft placed against a patch and/or the abdominal wall, pushing the handle 404 forward in the distal direction causes the shaft 402 to retract proximally into the handle as the drive tube 420 drives the suture anchor through the repair prosthetic and/or abdominal wall tissue.

To control retraction of the shaft, for example, to reduce the potential of inadvertent retraction of the shaft that may lead to premature exposure of the suture anchor, the instrument may include a shaft locking mechanism that secures the shaft 402 in one or more positions, including the distally extended position over the anchor. In one embodiment shown in FIG. 23-23A, the locking mechanism may include a lock 430 movably supported in the handle to engage and secure the shaft 402 in one or more positions, including the extended position. The lock 430 may include a projection 432 (FIG. 23A) that engages a corresponding feature, such as a notch 434, at a proximal end of the shaft to lock the shaft in the extended position. The lock may be coupled to a release trigger 436 adapted to disengage the lock from the notch 434 to allow the shaft to be retracted into the handle along the needle. The trigger 436 may be biased with a spring 438, such as a compression spring, to urge the lock into a locked position for engagement with the shaft. It is to be appreciated that other suitable lock arrangements may be employed as should be apparent to one of skill in the art.

The depth of penetration of the instrument for delivering the suture anchor may be controlled by limiting the amount of shaft retraction. As shown in FIG. 23, a stop 440 may be spaced in a proximal direction from the shaft coupling 428 and adapted to engage the coupling and/or another feature coupled to the shaft as the shaft is retracted to its fully retracted position to expose the anchor and drive element. The distance between the stop 440 and the coupling 428 or other feature may be selected to set the penetration of the drive element through tissue. In one embodiment, the instrument may be configured to limit penetration of the drive element to approximately 2 cm. Such an arrangement may be advantageous for delivering a suture anchor from within the abdominal cavity, through abdominal wall tissue opposite, and present the anchor on the opposite side of the fascia without penetrating the skin surface of the patient. However, it is to be understood that the instrument may be arranged to provide any amount of penetration using any suitable arrangement as should be apparent to one of skill in the art.

For some applications, the shaft 402 may include at least one additional feature, such as a distal notch, that engages with the lock when the shaft has been retracted a predetermined distance into the handle, which may correspond to a fully retracted position, to expose the needle. Such an arrangement may be advantageous to maintain the shaft in a retracted position without requiring a user to maintain a forward distal force against the abdominal wall.

The instrument may include a suture tensioning arrangement for tensioning the suture assembly so as to secure the soft tissue repair prosthetic against the abdominal wall. The suture tensioner may be housed within the elongated shaft 402 and may be operated with a tension mechanism included within and actuatable at the handle 404.

In one embodiment, the suture tensioner may include an elongated tube 442 or shaft that extends through and is movable within the drive tube 420. As shown in FIGS. 21-22, an end of the suture 414 extending from the suture anchor 416 may be retained in an opening 444, such as a keyhole or keyhole-like opening, provided along the tensioner tube. The suture tensioner 442 is retractable in a proximal direction within the drive tube 420 to pull the end of the suture in the proximal direction and draw the suture through the suture anchor 416.

As shown in FIG. 23, the tensioner 442 may extend through the handle 404 and be connected to a knob 446 at the proximal end of the handle that may be grasped and pulled by a user to retract the tensioner along the drive element to tension the suture. The amount of tension that may be exerted on the suture to tighten the suture assembly may be controlled by limiting the distance that the tensioner 442 may be retracted relative to the drive tube 420 as should be apparent to one of skill in the art. If desired, the tensioner 442 may be biased in the distal direction with a spring, such as a compression spring, in a manner as should be apparent to one of skill in the art.

The instrument may include a cutter or cutting arrangement for trimming excess suture following delivery and tightening of the suture assembly. In one illustrative embodiment shown in FIG. 22, the drive tube 420 may include a longitudinal slot 450 that is adapted to receive a portion of the suture 414 coupled to the tensioner 442. As shown, a proximal end portion 452 of the slot may be configured to taper down in the proximal direction to form a narrow end 454 that is adapted to cut or trim the suture. For example, and without limitation, the proximal end of the slot 450 may be provided with a cutting or shearing edge 456 that cooperates with the tensioner tube 442 to trim the suture. As the tensioner 442 is retracted within the drive tube 420, the end of the suture that is coupled to the tensioner is drawn in the proximal direction along and into the tapered cutter 452 which trims the suture when the suture assembly is tightened and the suture is drawn across the cutter edge. It is to be appreciated that other suture cutting arrangements are contemplated as should be apparent to one of skill in the art.

As indicated above, the instrument may include a tip 406 that is configured to support the suture assembly 410 at the distal end of the shaft. As shown in FIGS. 19-20, the tip may include an elongated slot 460 or opening with an open end to accommodate the suture anchor and suture extending from the anchor 416 to the force distribution member 412. The tip may also be configured to accommodate the force distribution member of the suture assembly. As shown in FIGS. 19 and 21, the tip may include a hole 462 that is adapted to receive and support a proximal end of the force distribution member during delivery of the suture assembly with the instrument. During retraction of the shaft 402, the tip 406 is retracted away from the suture anchor 416, which is supported at the distal end of the drive tube 420, causing the force distribution member 412 to be pulled from the hole 462 and separated from the tip 406 via the suture 414.

For some applications, the tip may be configured as a disposable unit that is preloaded with a suture assembly that can be attached to the shaft to load a suture assembly to the instrument and then released from the shaft after delivery of the suture assembly. In this manner, the handle, shaft and drive system of the instrument may be a reusable unit that can be reloaded with disposable tips. The shaft and tip may employ a releasable interface, as should be apparent to one of skill in the art, for attaching and releasing the tip. For example, and without limitation, the interface may include a snap-fit arrangement. It is also to be appreciated that the tip may be permanently fixed to the shaft and the instrument can be reloaded, if desired, with one or more suture assemblies using other techniques as should be apparent to one of skill in the art.

In one illustrative embodiment shown in FIG. 24, the suture assembly 410 may employ a ratchet-like arrangement that permits the suture anchor to move only in a direction toward the force distribution member. In one embodiment, the suture assembly may include a suture 414 having a plurality of barbs 470 or barb-like features spaced along at least a portion of its length that allow relative movement between the suture 414 and the anchor 416 in one direction while preventing relative movement therebetween in the opposite direction. The anchor 416 may be configured to coact with the barbed suture for tightening the suture assembly.

The suture anchor 416 may include an elongated body 472 with a transverse throughbore 474 for receiving the suture 414 therethrough so that the location of the suture anchor is selectively variable relative to the suture to tighten the suture assembly. The body may include a proximal portion 476 that is configured to be received within the distal end of the drive tube 420 with a larger distal portion 478 that is configured to extend from the distal end of the drive tube. As indicated above, the suture anchor may include a pointed distal tip 418 that is adapted to penetrate a soft tissue repair prosthetic and/or abdominal wall tissue as the anchor is pushed therethrough with the drive system.

A toggle arm 480 may extend radially outward and in a generally axial direction beyond the proximal end of the body. The toggle arm may be configured to engage tissue or muscle and so as to prevent the anchor from being drawn back through the needle hole in the tissue and to help toggle or rotate the anchor 416 as the suture assembly is tightened.

To prevent the suture from slipping out of the anchor body, an end 482 of the suture may be knotted, formed in a bulbous shape, or otherwise configured so as not to pass through the anchor. The enlarged end 482 of the suture is also configured to couple the suture to the tensioner 442, as described above.

It is to be appreciated that the suture anchor is not limited to the shape with a toggle arm as shown and may have other configurations suitable for penetrating tissue, tightening and anchoring an end of the suture, as should be apparent to one of skill in the art.

As shown in FIG. 24, the force distribution member 412 may include a body 484 with a substantially cylindrical configuration, such as a T-bar configuration suitable for spreading forces applied along the suture when the suture assembly is tightened against a repair patch or the abdominal wall. The body may include a distal portion 486 with an axial throughbore 488 that cooperates with a transverse bore 490 for receiving the suture 414 therethrough. The body also includes a proximal portion 492 that is configured to be received in the hole 462 provided in the tip to support the force distribution member on the instrument. A shoulder 494 may be provided between the proximal and distal portions to limit the depth of insertion of the force distribution member into the tip.

It is to be appreciated that the force distributing member is not limited to the tubular shape shown, as should be apparent to one of skill in the art, and may have other configurations including, but not limited to, configurations such as those described above for the suture assembly shown in FIG. 4.

The force distribution member 412 may be attached to an end of the suture by threading an end portion of the suture through the transverse 490 and axial 488 bores. To prevent the suture from slipping out of the anchor body, an end 496 of the suture may be knotted, formed in a bulbous shape, or otherwise configured so as not to pass through the force distribution member. It is to be understood that the force distributing member may be attached to the suture using other suitable arrangements as should be apparent to one of skill in the art including, but not limited to, the various techniques described above in connection with the suture assembly of FIG. 4.

The suture anchor and the force distributing member for the described suture assemblies may be formed of a permanent material (e.g., polypropylene, polycarbonate, nylon, polyester, stainless steel, titanium), an absorbable material (e.g., polyglycolic acid (PGA), polylactic acid (PLA), polydioxanone (PDO), and blends of any of the foregoing), or a hybrid of a permanent material and an absorbable material.

The suture for the described suture assemblies may be formed of a synthetic or natural material, and may be absorbable or non-absorbable. For some applications, the suture may be formed of a stretchable material. Representative suture materials include, but are not limited to, polypropylene, PTFE, nylon, polyester, polybutester, silk, PGA, PLA/PGA, caprolactone, catgut, polyhydroxyalkanoate and PDO.

An illustrative method of delivering a transfascial suture using the instrument 600 will be described in connection with FIGS. 25-27.

Figure 25:
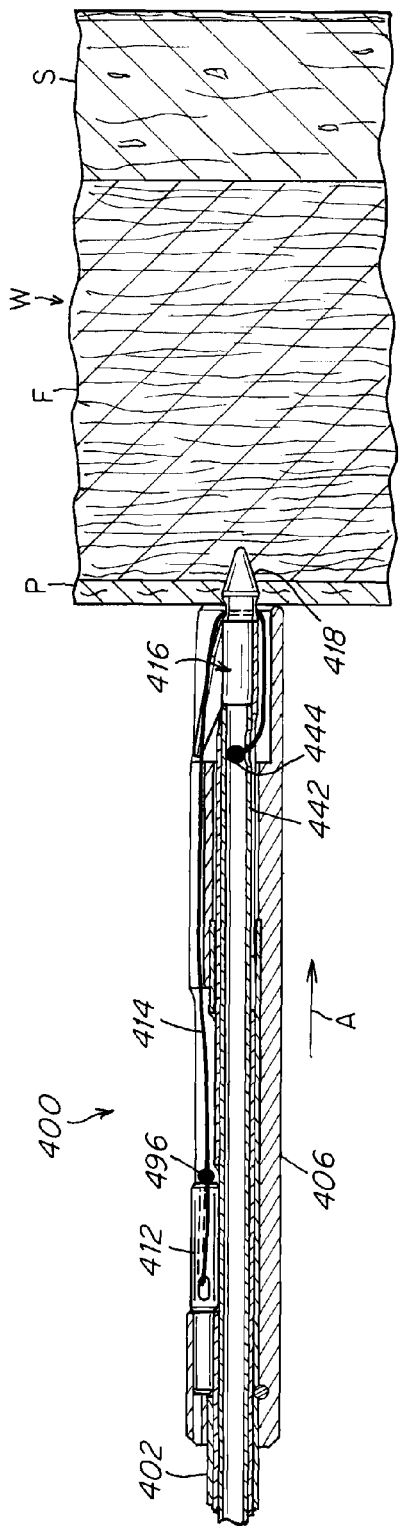
FIGS. 25-27 illustrate a method of transfascial suturing using the instrument and suture assembly of FIGS. 18-24.

As shown in FIG. 25, the instrument may be inserted into the abdominal cavity with the distal tip 418 of the suture anchor 416 protruding from the distal end of the shaft to facilitate locating the instrument against the abdominal wall patch P and/or abdominal wall W. However, if desired, the instrument may be configured for insertion in a sharps-free condition with the anchor housed fully within the shaft.

Following placement of the instrument within the abdominal cavity at a desired location against the abdominal wall patch P and/or wall, the shaft 402 may be unlocked by actuating the release trigger 436 which disengages the lock 430 from the shaft.

Figure 26:
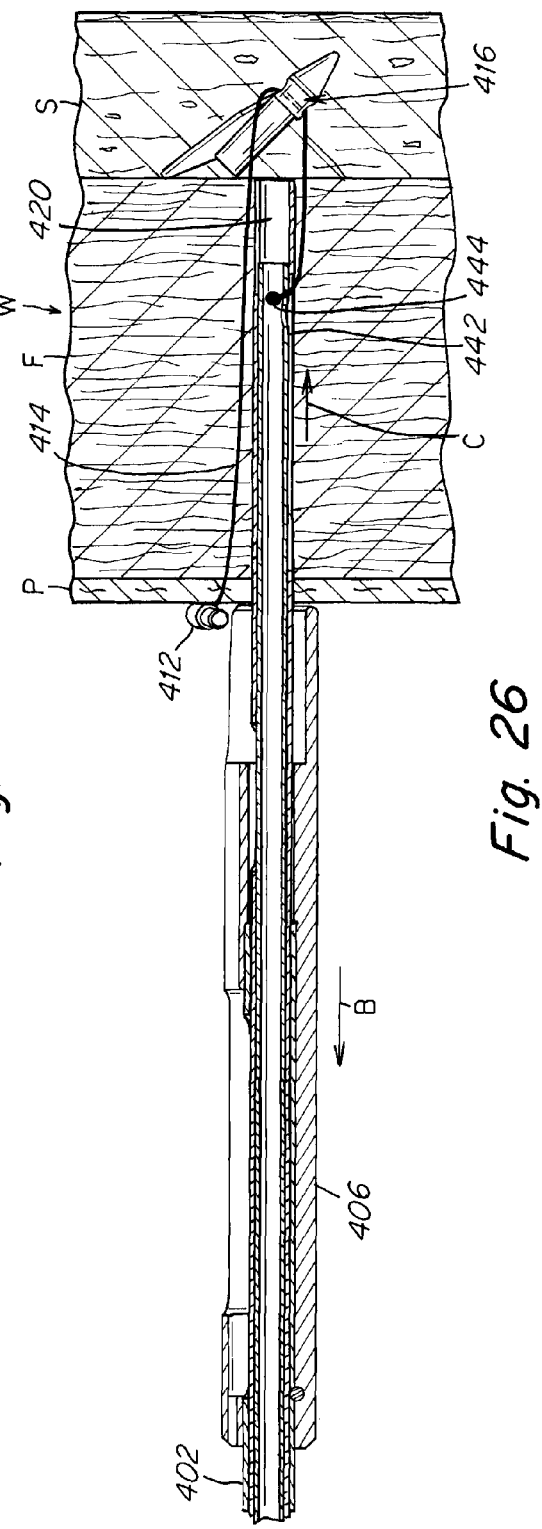
Figure 27:
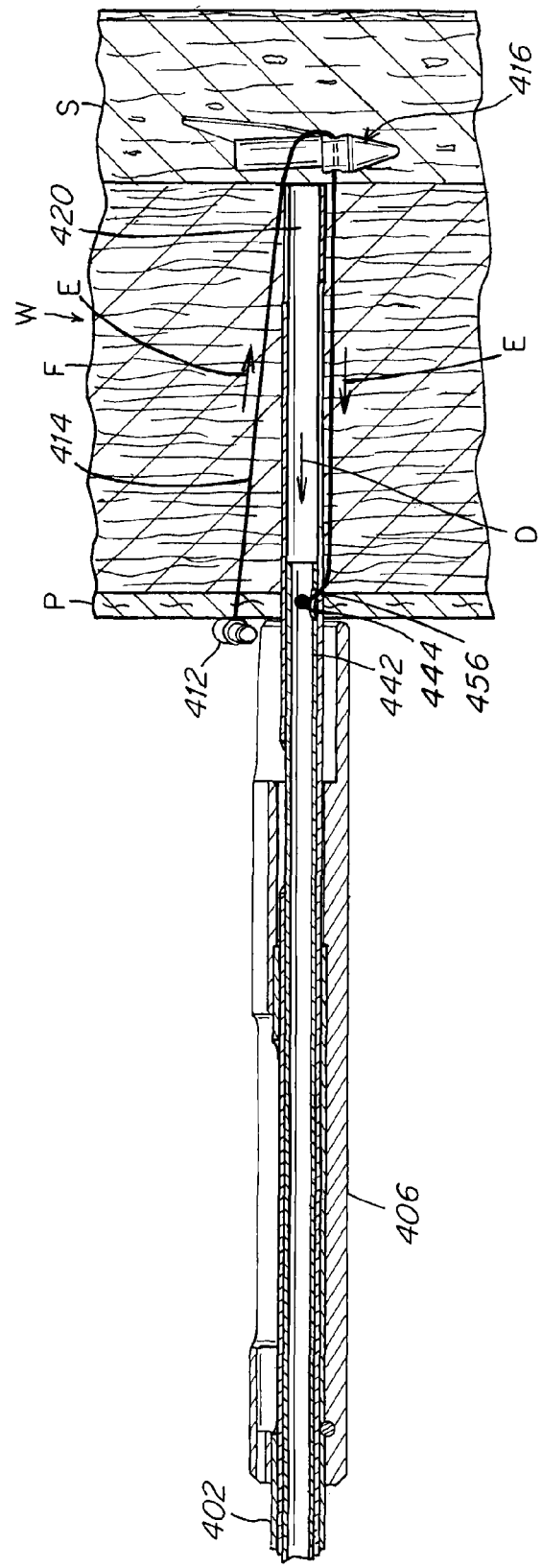

As shown in FIG. 26, with the shaft unlocked, the instrument may be pushed in the distal direction (arrow A) against the abdominal wall patch P and/or wall W causing the shaft 402 to retract (arrow B) into the handle as the anchor 416 is driven through a portion of the abdominal wall W with the drive tube 420 (arrow C). When the shaft becomes fully retracted, distal advancement of the instrument ceases with the anchor being presented on the opposite side of the fascia F with no penetration of the skin surface S. As the shaft is retracted during advancement of the suture anchor through the fascia, the force distribution member 412 is pulled by the suture 414 coupled to the anchor 416 and also becomes separated from the instrument.

As shown in FIG. 26, the suture anchor 416 is then separated from the instrument. Separation may occur by partially retracting the instrument through the fascia. If desired, the tensioner 442 may be extended distally to push and dislodge the anchor 416 from the drive tube.

With the suture anchor located between the fascia F and the skin surface S, the suture assembly may be tightened to secure the patch P in position against the abdominal wall W. As shown in FIG. 27, the suture assembly is tightened by retracting the suture tensioner 442 in a proximal direction (arrow D) which pulls (arrows E) the suture 414 through the anchor 416 and draws the force distribution member 412 against the patch P. The suture anchor and force distribution member may toggle or rotate into anchoring positions against the fascia and patch during tightening of the suture assembly.

When the suture assembly is sufficiently tightened, excess suture may be cut or trimmed below the skin surface. As shown in FIG. 27, the suture 414 may be trimmed by drawing an end portion of the suture across a cutter as the suture is pulled proximally with the tensioner 442.

The above described method may be repeated to provide additional suture fixation points through the abdominal wall patch and/or fascia as desired by the surgeon for carrying out the particular repair procedure.

A method of transfascial suturing, for example in the repair of an abdominal wall defect such as a ventral hernia, will now be described. The patient is prepared in the typical fashion for hernia surgery which may include administration of general anesthesia, identification of the hernia size and location, and shaving, washing and sterilization of the surgical site. The abdominal cavity may be insufflated or otherwise expanded to separate the abdominal wall from organs located in the abdominal cavity. A trocar cannula may be inserted to provide camera access to the cavity allowing the physician to visualize the surgical site. A separate laparoscopic cannula may be inserted into the abdominal wall cavity, or an incision (such as formed by a trocar) may be made leading into the abdominal wall cavity, and an abdominal wall repair prosthetic then may be inserted, as described below, through such cannula, incision, or other passageway into the abdominal cavity.

Figure 28:
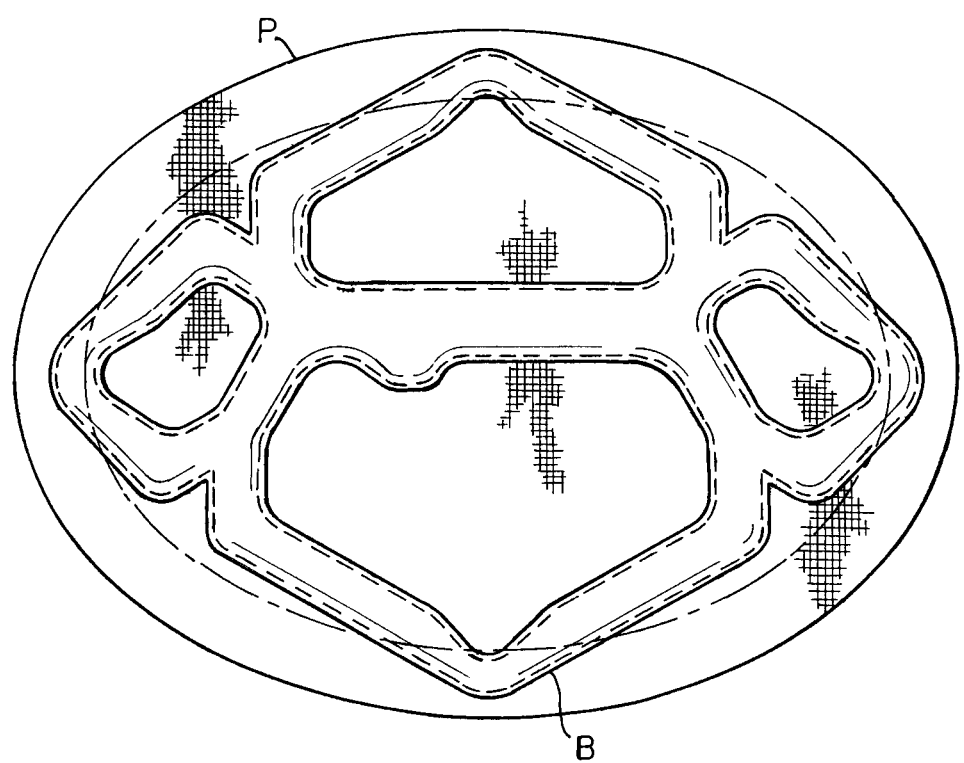
FIG. 28 is an illustration of a ventral repair patch and an inflatable deployment assist device.

The prosthetic, which may be in the form of a patch, preferably is reduced in size to facilitate delivery through the slender cannula or incision. For example, and without limitation, the prosthetic may be rolled, folded, or otherwise collapsed into a shape suitable for passage through the narrow approach to the abdominal cavity. Once located within the cavity, the prosthetic is unfurled or otherwise enlarged, manually or inherently under its own power, and then is positioned relative to the defect, preferably with a margin of at least several centimeters projecting beyond the edges of the defect. Delivery and enlargement of the patch may be facilitated by a mesh introducer such as a PRECISIONPASS instrument available from Davol Inc., assignee of the instant application. Alternatively, a patch deployment assist device, such as an inflatable deployment assist balloon B as illustrated in FIG. 28, may be employed to deliver, expand, and/or position the prosthetic P against the abdominal wall relative to the defect.

In a representative method, the patch P is reduced along with a deflated deployment assist device B, to a slender size such as by rolling the patch and deployment assist device into a cylindrical shape. One or more attachment components on the deployment assist device may help mount the patch to the deployment assist device. An inflation tube for the deployment assist device may be routed through the patch and then grasped, once the deployment assist device and patch are in the abdominal cavity, by a grasper or other instrument that has been inserted into the abdominal cavity from outside of the patient. The grasper is withdrawn, externalizing the inflation tube. The end of the inflation tube outside of the patient may be fluidly connected to an inflation source. Introduction of an inflation medium through the inflation tube will expand the balloon, unfurling the patch into a substantially planar configuration or such other end-use configuration as may be desired. The patch is positioned relative to the defect and when appropriately located, the inflation tube may be pulled from outside of the patient to hoist the deployment assist device and, consequently, the patch carried thereby against the abdominal wall. A hemostat, clamp or other instrument, may be applied to the inflation tube to retain the deployment assist device in position. If desired, the patch still may be rotated to optimize angular orientation of the patch.

The prosthetic patch may be maintained in position against the abdominal wall by the deployment assist device or, alternatively, by use of laparoscopic instruments such as graspers. At this time, in the discretion of the physician, a plurality of coils, tacks, staples, or other mechanical fixation elements may be applied through the patch into the abdominal wall.

An instrument for delivering suture is then inserted through the cannula or narrow incision into the abdominal cavity. The instrument may be preloaded with a suture assembly or a suture assembly may be loaded by the physician or other user. From within the abdominal cavity and under camera visualization, the tip of the suture delivery instrument is placed against a margin of the patch, or other location as desired by the physician.

At least one trigger or other control is actuated, from outside of the patient, driving a needle or drive element through the distal end of the instrument. The needle advances out of the instrument, either in a single full stroke or in partial strokes, and pierces through the patch margin, the abdominal wall (fascia) and, if desired, also through subcutaneous tissue, fat and skin, with the needle delivering a suture anchor and suture through the patch and anatomy. Alternatively, an instrument with a retractable outer shaft may be employed to control penetration of a drive element and suture anchor through the fascia so as to present the anchor on the opposite side of the fascia and below the skin surface abdominal wall from inside the abdominal cavity. Once deployed, each suture assembly may be tightened to hoist and/or secure the patch against the abdominal wall.

As the suture assembly is tightened, either externally or subdermally from within the abdominal cavity, a suture force distribution member becomes lodged against the prosthetic inside of the abdominal wall cavity. Advantageously, the puncture openings through the patch formed by the needle or drive element may be covered, at least in part, by the force distribution member. By covering the puncture openings, the suture force distribution member helps prevent adhesions between the viscera and the tissue infiltratable side of the patch. The delivery, tightening and trimming of suture assembles may be repeated, for example at spaced locations about the periphery of the patch. Any skin punctures may be closed by stitching, adhesive strip or otherwise.

The deployment assist device may be separated from the patch and removed at any time after proper positioning of the patch, and preferably after the patch has at least been provisionally secured such as by initial suturing or mechanical fixation, and may remain in the abdominal cavity until transfascial suturing has been completed. As mentioned, mechanical fixation elements may, at the discretion of the physician, be applied to the patch prior to transfascial suturing. Alternatively, such mechanical fixation may occur after transfascial suturing, or the transfascial suturing procedure may be concluded without deploying any mechanical fixation elements.

The soft tissue repair prosthetic may be formed of a porous material, such as a knit, woven or non-woven fabric, or may be composed of a solid, substantially non-porous, or microporous material. The prosthesis may be formed of one or more layers of the same or dissimilar material, and the layers may be stacked one on top of the other, side-to-side, or include a combination of both stacking arrangements. The prosthesis may be formed with portions that are tissue infiltratable and other portions that are less tissue infiltratable or are non-tissue infiltratable, providing selected areas of the repair device with different tissue ingrowth and adhesion resistant properties. The prosthesis may be formed of permanent material, resorbable material, or a combination of permanent and resorbable materials. It should be appreciated that the prosthesis may be formed of any biologically compatible material, synthetic or natural, suitable for repairing a tissue or muscle wall defect as would be apparent to one of skill in the art. Depending upon the surgical application, the prosthesis may be in the form of a patch, plug or combination patch and plug.

In a representative embodiment, the soft tissue repair prosthetic is in the form of a ventral hernia repair patch, and may include a tissue infiltratable layer and a barrier layer. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. In the described method of ventral hernia repair, the polypropylene side would face the abdominal wall and the ePTFE side would face the viscera.

Surgical materials which are suitable for tissue or muscle reinforcement and defect correction may be utilized include, but are not limited to, BARD MESH (available from C.R. Bard, Inc.), SOFT TISSUE PATCH (microporous ePTFE—available from W. L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Biologic materials, including XENMATRIX, COLLAMEND, and ALLOMAX (all available from C.R. Bard, Inc.) or COOK SURGISIS (available from Cook Biomedical, Inc.) may also be used. Resorbable materials, including polyglactin (VICRYL—available from Ethicon, Inc.) and polyglycolic acid (DEXON—available from US Surgical, Inc.). These materials may be used alone in a soft tissue repair prosthetic, in combination with one another, or in combination with other materials. The fabric may be formed from multifilament yarns and any suitable method, such as knitting, weaving, braiding, molding and the like, may be employed to form the mesh material. It should be appreciated that when the soft tissue repair prosthesis is in the form of a patch, it may be configured in many shapes, including, but not limited to substantially flat, concave, convex, and concave-convex, and may, for example, be in the shape of a square, rectangle, circle, or ellipse. Further, the patch may be loaded with one or more drugs including, without limitation, an analgesic or antibiotic.

The above and other aspects of the invention will be appreciated from the detailed description and claims. It should be understood that although aspects of the invention have been described with reference to illustrative embodiments, aspects of the invention are not limited to the embodiments described. Also, aspects of the invention may be used alone, or in any suitable combination with other aspects of the invention.

The invention claimed is:

1. A method of transfascial suturing, the method comprising acts of:
   (a) delivering a suture assembly into an abdominal cavity of a patient, the suture assembly including a movable suture anchor, a force distribution member and a suture connected to the movable suture anchor and the force distribution member, the movable suture anchor being movable along a length of the suture;
   (b) after act (a), passing the movable suture anchor, from within the abdominal cavity, through a soft tissue repair prosthetic provided in the abdominal cavity and then through the abdominal wall to a location above the skin surface with the force distribution member being maintained in the abdominal cavity; and
   (c) after act (b), tightening the suture assembly by advancing the movable suture anchor along the suture from above the skin surface to a position below the skin surface.

2. The method according to claim 1, wherein act (c) includes positioning the movable suture anchor between fascia and the skin layer.

3. The method according to claim 1, wherein act (b) includes positioning the force distribution member against the soft tissue repair prosthetic.

4. The method according to claim 1, wherein act (c) includes tightening the suture between the movable suture anchor and the force distribution member.

5. The method according to claim 1, wherein act (c) includes adjusting the relative position of the movable suture anchor and the force distribution member.

6. The method according to claim 1, wherein act (c) includes pulling a portion of the suture extending outside the abdominal cavity and above the skin surface.

7. The method according to claim 1, wherein act (c) includes advancing the movable suture anchor along the suture with an anchor pusher.

8. The method according to claim 1, further comprising an act (d) of trimming excess suture below the skin surface.

9. The method according to claim 1, wherein act (b) includes passing the movable suture anchor in a first orientation through the abdominal wall and act (c) includes reorienting the movable suture anchor to a second orientation.

10. The method according to claim 1, wherein act (a) includes inserting a suturing instrument into the abdominal cavity, the suturing instrument loaded with the suture assembly.

11. The method according to claim 1, wherein act (b) includes piercing the soft tissue repair prosthetic and then piercing the abdominal wall.

12. The method according to claim 1, further comprising repeating acts (b) and (c) in one or more locations about a peripheral segment of the soft tissue repair prosthetic.

13. The method according to claim 1, wherein the soft tissue repair prosthetic is in the form of a patch.

14. The method according to claim 1, further comprising, before act (b), non-suture fixating the soft tissue repair prosthetic to the abdominal wall.

15. The method according to claim 14, wherein the act of non-suture fixating includes one or more acts of tacking, screw fastening or helicoil fastening the soft tissue repair prosthetic to the abdominal wall.

16. The method according to claim 1, further comprising after act (b), non-suture fixating the soft tissue repair prosthetic to the abdominal wall.

17. The method according to claim 16, wherein the act of non-suture fixating includes one or more acts of tacking, screw fastening or helicoil fastening the soft tissue repair prosthetic to the abdominal wall.

18. The method according to claim 1, further comprising, before act (b), an act (e) of inserting a deployment assist device into the abdominal cavity and positioning, with the deployment assist device, the soft tissue repair prosthetic against the abdominal wall.

19. The method according to claim 18, wherein act (e) includes mounting the soft tissue repair prosthetic to the deployment assist device before inserting the deployment assist device into the abdominal cavity.

20. The method according to claim 18, wherein the deployment assist device is inflatable.

21. The method according to claim 1, wherein act (b) includes associating the movable suture anchor with a needle and passing the needle with the movable suture anchor through the soft tissue repair prosthetic and at least part of the abdominal wall.

22. A method of transfascial suturing, the method comprising acts of:

(a) delivering a suture assembly into an abdominal cavity of a patient, the suture assembly including a suture anchor, a force distribution member and a suture connected to the suture anchor and the force distribution member;

(b) passing the suture anchor, from within the abdominal cavity, through a soft tissue repair prosthetic provided in the abdominal cavity and then through at least a portion of the abdominal wall to a location below the skin surface without penetrating the skin surface and with the force distribution member being maintained in the abdominal cavity; and (c) tightening the suture assembly by pulling the suture through the suture anchor to draw the force distribution member toward the soft tissue repair prosthesis.

23. The method according to claim 22, wherein act (b) includes positioning the force distribution member against the soft tissue repair prosthetic.

24. The method according to claim 22, wherein act (c) includes tightening the suture between the suture anchor and the force distribution member.

25. The method according to claim 22, wherein act (c) includes pulling a portion of the suture located below the skin surface without penetrating the skin surface.

26. The method according to claim 25, wherein act (c) includes pulling the portion of the suture located below the skin surface in a direction toward the abdominal cavity.

27. The method according to claim 22, further comprising an act (d) of trimming excess suture within the abdominal wall.

28. The method according to claim 22, wherein act (b) includes passing the suture anchor in a first orientation through the abdominal wall and act (c) includes reorienting the suture anchor to a second orientation.

29. The method according to claim 22, further comprising repeating act (b) in one or more locations about a peripheral segment of the soft tissue repair prosthetic.

30. The method according to claim 22, wherein the soft tissue repair prosthetic is in the form of a patch.

31. The method according to claim 22, further comprising, before act (b), non-suture fixating the soft tissue repair prosthetic to the abdominal wall.

32. The method according to claim 31, wherein the act of non-suture fixating includes one or more acts of tacking, screw fastening or helicoil fastening the soft tissue repair prosthetic to the abdominal wall.

33. The method according to claim 22, further comprising after act (b), non-suture fixating the soft tissue repair prosthetic to the abdominal wall.

34. The method according to claim 33, wherein the act of non-suture fixating includes one or more acts of tacking, screw fastening or helicoil fastening the soft tissue repair prosthetic to the abdominal wall.

35. The method according to claim 22, further comprising, before act (b), an act (e) of inserting a deployment assist device into the abdominal cavity and positioning, with the deployment assist device, the soft tissue repair prosthetic against the abdominal wall.

36. The method according to claim 35, wherein act (e) includes mounting the soft tissue repair prosthetic to the deployment assist device before inserting the deployment assist device into the abdominal cavity.

37. The method according to claim 35, wherein the deployment assist device is inflatable.

\* \* \* \* \*